United States Patent [19]
Fritz et al.

[11] Patent Number: 5,514,802
[45] Date of Patent: May 7, 1996

[54] INTERMEDIATES FOR PREPARING HIV PROTEASE INHIBITORS

[75] Inventors: James E. Fritz, Greenwood, Ind.; Marlys Hammond, Pasadena, Calif.; Stephen W. Kaldor, Indianapolis, Ind.

[73] Assignee: Eli Lilly and Company, Indianapolis, Ind.

[21] Appl. No.: 416,568

[22] Filed: Apr. 4, 1995

Related U.S. Application Data

[62] Division of Ser. No. 994,871, Dec. 22, 1992, Pat. No. 5,434,265.

[51] Int. Cl.⁶ .................................................. C07D 217/16
[52] U.S. Cl. ............................................. 546/146; 564/162
[58] Field of Search ............................ 564/146, 162

[56] References Cited

U.S. PATENT DOCUMENTS 5,142,056  8/1992  Kempe et al. ........................... 546/264

FOREIGN PATENT DOCUMENTS

| | | |
|---|---|---|
| 0337714 | 10/1989 | European Pat. Off. . |
| 0346847 | 12/1989 | European Pat. Off. . |
| 0361341 | 4/1990 | European Pat. Off. . |
| 0402646 | 12/1990 | European Pat. Off. . |
| 0432695 | 6/1991 | European Pat. Off. . |
| 0533342 | 3/1993 | European Pat. Off. . |
| 0526009 | 2/1993 | European Pat. Off. . |
| WO A 92 08701 | 5/1992 | WIPO . |

OTHER PUBLICATIONS

Roberts, N.A. et al., Science, 248, 358–361 (1990).

Vara Prasad, J.V.N. et al., Peptides, Chemistry and Biology, Proceeding of the Twelfth American Peptides Symposium, Jun. 16–21, 721–722 (1990).

Thaisrivongs, S. et al., J. Med Chem, 34, 2344–2356 (1991).

*Primary Examiner*—Bernard Dentz
*Attorney, Agent, or Firm*—Janet T. McClain

[57] ABSTRACT

The present invention provides novel HIV protease inhibitors, pharmaceutical formulations containing those compounds and methods of treating and/or preventing HIV infection and/or AIDS.

1 Claim, No Drawings

INTERMEDIATES FOR PREPARING HIV PROTEASE INHIBITORS

This application is a division of application Ser. No. 07/994,871 filed Dec. 22, 1992, now U.S. Pat. No. 5,434,265.

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III and Visna Virus, A Pathogenic Lentivirus", Science, 227, 173, (1985); P. Sonigo, N. Alizon, et al., "Nucleotide Sequence of the Visna Lentivirus: Relationship to the AIDS virus", Cell, 42, 369, (1985). The complex disease AIDS includes progressive destruction of the immune system and degeneration of the central and peripheral nervous system. The HIV virus was previously known or referred to as LAV, HTLV-III or ARV.

A common feature of retrovirus replication is the post-translational processing of precursor polyproteins by a virally encoded protease to generate mature viral proteins required for viral assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment or prevention of AIDS and the treatment or prevention of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, the currently used therapeutic, AZT, is an inhibitor of the viral reverse transcriptase. H. Mitsuya, N. S. Broder, "Inhibition of the In Vitro Infectivity in Cytopathic Effects of HTLV III", Proc. Natl. Acad. Sci. U.S.A., 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known compounds suffer from toxicity problems, lack of bioavailability or short in vivo half-lives. Thus, despite the recognized therapeutic potential associated with a protease inhibitor and the research efforts expended thus far, a viable therapeutic agent has not yet emerged.

Accordingly, a primary object of the present invention is to provide novel protease inhibitors which are useful in the treatment or prevention of HIV infection and/or the resulting acquired immune deficiency syndrome (AIDS).

A further object of the present invention is to provide therapeutic compositions that are of value in the treatment or prevention of HIV invention and/or AIDS.

Still another object is to provide methods for the treatment or prevention of HIV infection and/or AIDS.

Other objects, features and advantages will become apparent to those skilled in the art from the following description and claims.

SUMMARY OF THE INVENTION

The present invention relates to compounds of formula I, below, and pharmaceutically acceptable salts thereof that inhibit the protease encoded by human immunodeficiency virus (HIV) type 1 (HIV-1) and type 2 (HIV-2). These compounds are useful in the treatment or prevention of infection by HIV and the treatment or prevention of the resulting acquired immune deficiency syndrome (AIDS). The compounds, their pharmaceutically acceptable salts, and the pharmaceutical compositions can be used alone or in combination with other antivirals, immunomodulators, antibiotics or vaccines. Methods of treating or preventing AIDS, methods of treating or preventing HIV infection and methods of inhibiting HIV replication are disclosed.

The present invention relates to a method of inhibiting HIV protease in an HIV infected cell, a cell susceptible to HIV infection or a primate in need thereof, thus treating or preventing HIV infection and/or AIDS, comprising administering an effective amount of a compound of formula I

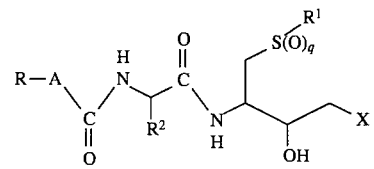

wherein:

R is aryl, heterocycle or unsaturated heterocycle;

A is a bond, —$(CH_2)_v$—, —$(CH_2)_m$—O—$(CH_2)_n$— or —$(CH_2)_m NR^0$—$(CH_2)_n$—, where
  m and n are independently 0, 1 or 2;
  v is 0, 1, 2 or 3;
  $R^0$ is hydrogen or $C_1$–$C_4$ alkyl;

q is 0, 1 or 2;

$R^1$ is aryl or $C_5$–$C_7$ cycloalkyl;

$R^2$ is an amino acid side chain, —$CH_2$—$R^{2a}$, —$CH_2$—C(O)—$NR^0$—A—$R^{2a}$ or —$CH_2$—C(O)—$OR^{2a}$, where
  $R^{2a}$ is aryl, heterocycle or unsaturated heterocycle;

X is a group having the structure:

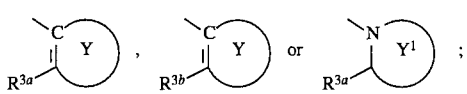

Y is aryl or unsaturated heterocycle;

$Y^1$ is heterocycle;

$R^{3a}$ is a group having the structure:

1) —C(O)—$NR^4R^4$,

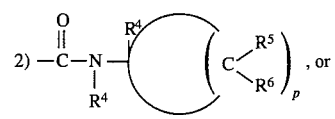

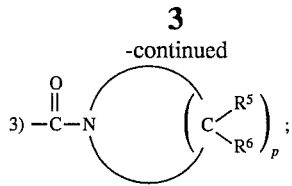

$R^{3b}$ is a group having the structure:

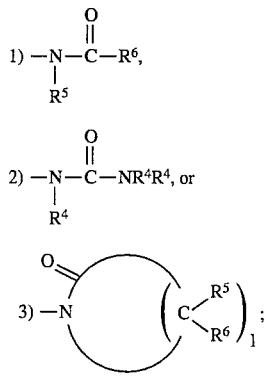

where:

p is 4 or 5;

l is 3, 4 or 5;

$R^4$ at each occurrence is independently hydrogen, $C_1$–$C_6$ alkyl or hydroxy($C_1$–$C_4$)alkyl; and $R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy($C_1$–$C_4$)alkyl, carboxy, $C_1$–$C_4$ alkoxycarbonxyl, carbamoyl, N—($C_1$–$C_4$)alkylcarbamoyl, aryl, heterocycle or unsaturated heterocycle;

or a pharmaceutically acceptable salt thereof.

The present invention also relates to a compound of formula I, or a pharmaceutically acceptable salt thereof, wherein A, R, $R^1$, $R^2$, q and X are as defined above.

The present invention further provides pharmaceutical formulations comprising a compound of the present invention, or a pharmaceutically acceptable salt thereof, in combination with a pharmaceutically acceptable carrier, diluent or excipient therefor.

A further embodiment of the present invention is a class of novel intermediates useful for preparing the compounds of formula I. The intermediates have the formula IA

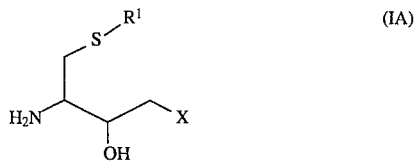

where $R^1$ and X are as defined above for formula I;

or a pharmaceutically acceptable salt thereof.

DETAILED DESCRIPTION OF THE INVENTION

The present invention provides new compounds of formula I, as described above, that are useful for treating or preventing HIV infection and/or AIDS.

All temperatures stated herein are in degrees Celsius (° C.). All units of measurement employed herein are in weight units except for liquids which are in volume units.

As used herein, the term "$C_1$–$C_6$" represents a straight or branched alkyl chain having from one to six carbon atoms. Typical $C_1$–$C_6$ groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl".

"Halo" represents a chloro, fluoro, bromo or iodo.

"Halo($C_1$–$C_4$)alkyl" represents a straight or branched alkyl chain having from one to four carbon atoms with 1–3 halogen atoms attached to it. Typical halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

"Cyano($C_{1-4}$)alkyl" represents a straight or branched alkyl chain having from one to four carbon atoms with a cyano group attached to it. Typical cyano($C_1$–$C_4$)-alkyl group include cyanomethyl, 2-cyanoethyl, 3-cyanopropyl, 2-cyanoisopropyl, 4-cyanobutyl and the like.

"$C_1$–$C_4$ alkylthio" represents a straight or branched alkyl chain having from one to four carbon atoms attached to a sulfur atom. Typical $C_1$–$C_4$ alkylthio groups include methylthio, ethylthio, propylthio, isopropylthio, butylthio and the like.

"$C_1$–$C_4$ alkylthio($C_1$–$C_4$)alkyl" represents a straight or branched alkyl chain containing from one to four carbon atoms with a $C_1$–$C_4$ alkylthio group attached to it. Typical $C_1$–$C_4$ alkylthio($C_1$–$C_4$)alkyl groups include methylthioethyl, ethylthiobutyl, propylthioisopropyl, isopropylthioethyl, butylthioethyl and the like.

"$C_1$–$C_4$ alkylamino" represents a straight or branched alkylamino chain having from one to four carbon atoms branched to an amino group. Typical $C_1$–$C_4$ alkylamino groups include methylamino, ethylamino, propylamino, isopropylamino, butylamino, sec-butylamino and the like.

"Di($C_1$–$C_4$)alkylamino" represents a straight or branched dialkylamino chain having two alkyl chains of from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

"$C_1$–$C_4$ alkoxy" represents a straight or branched alkyl chain having from one to four carbon atoms attached to an oxygen atom. Typical $C_1$–$C_4$ alkoxy groups include methoxy, ethoxy, propoxy, isopropoxy, butoxy and the like.

"$C_1$–$C_4$ alkoxycarbonyl" represents a straight or branched alkoxy chain having from one to four carbon atoms attached to a carbonyl moiety. Typical $C_1$–$C_4$ alkyoxycarbonyl groups include methoxycarbonyl, ethoxycarbonyl, propoxycarbonyl, isopropoxycarbonyl, butoxycarbonyl, t-butoxycarbonyl and the like.

"Carbamoyl($C_1$–$C_4$)alkyl" represents a straight or branched alkyl chain having from one to four carbon atoms with a carbamoyl group attached to it. Typical carbamoyl($C_1$–$C_4$)alkyl groups include carbamoylmethyl, carbamoylethyl, carbamoylpropyl, carbamoylisopropyl, carbamoylbutyl and carbonate-t-butyl and the like.

"$C_5$–$C_7$ cycloalkyl" represents a saturated hydrocarbon ring structure containing from five to seven carbon atoms which is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —($CH_2$)$_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical $C_5$–$C_7$ cycloalkyl groups include cyclopentyl, cyclohexyl, cycloheptyl, 3-methylcyclopentyl, 4-ethoxycyclohexyl, 5-carboxycycloheptyl, 6-chlorocyclohexyl and the like.

The term "heterocycle" represents and unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached to any heteroatom or carbon atom which affords a stable structure. The heterocycle is unsubstituted or substituted with 1, 2 or 3 substituents independently selected from halo, halo($C_1$–$C_4$)-alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamimo or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

The term "unsaturated heterocycle" represents an unsubstituted or substituted stable 5- to 7-membered monocyclic or 7- to 10-membered bicycle heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which nay of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazole, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinysulfone, oxadiazolyl, triazolyl, tetrahydroquinolinyl, tetrahydrisoquinolinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl 4-methylisoquinolinyl, 6,8-dibromoquinolinyl, 4,8-dimethylnaphthyl, 2-methyl-1,2,3,4-tetrahydroisoquinolinyl, N-methylquinolin-2-yl, 2-t-butoxycarbonyl-1,2,3,4-isoquinolin-7-yl and the like.

"Aryl" represents a phenyl or naphthyl ring which is optionally substituted with 1, 2 or 3 substituents independently selected from halo, morpholino($C_1$–$C_4$)alkoxycarbonyl, pyridyl($C_1$–$C_4$)alkoxycarbonyl, $C_1$–$C_4$ alkyl, $C_1$–$C_4$ alkoxy, carboxy, $C_1$–$C_4$ alkoxycarbonyl, carbamoyl, carbamoyl($C_1$–$C_4$)alkyl, amino, $C_1$–$C_4$ alkylamino, di($C_1$–$C_4$)alkylamino or a group of the formula —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical aryl groups include 4-methylphenyl, 3-ethylnaphthyl, 2,5-dimethylphenyl, 8-chloronaphthyl, 3-aminonaphthyl, 4-carboxyphenyl and the like.

The term "amino acid side chain" represents the distinctive atom or group bonded to an α-carbon atom also having bonded thereto a carboxyl group and an amino group. These side chains are selected from those found on the following amino acids:

| | |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl or urethane-type blocking groups such as benzyloxycarbonyl, 4-phenylbenzyloxycarbonyl 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methysulfonyl)ethoxycarbonyl, 2-(triphenylphosphino)-ethoxycarbonyl, fluorenylmethoxcarbonyl ("FMOC") 2-trimethylsilyl)ethoxycarbonyl, allyloxycarbonyl, 1-(trimethysilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; or benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc) and benzyloxycarbonyl (Cbz). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxy-benzhydryl, t-butyl, t-amyl, trityl, 4-methoxytrityl, 4,4'-dimethoxytrityl, 4,4'4"-trimethoxytrityl, 2-phenylprop-2-yl, trimethylsilyl, t-butyldimethylsilyl, phenacyl, 2,2,2-trichloroethyl, β-(di(butyl)methylsilyl)ethyl, p-toluenesulfonylethyl, 4-nitrobenzylsulfonylethyl, allyl, cinnamyl, 1-(trimethylsilylmethyl)prop-1-en-3-yl and the like moieties. A preferred carboxy-protecting group is benzhydryl. Further examples of these groups are found in E. Haslam, "Protective Groups in Organic Chemistry", J. G. W. McOmie, E., Plenum Press, New York, N.Y. 1973, Chapter 5, and T. W. Greene, "Protective Groups in Organic Synthesis", John Wiley and Sons, New York, N.Y., 1981, Chapter. 5.

The compounds of the present invention have at least three asymmetric centers as denoted by the asterisks in the formula below.

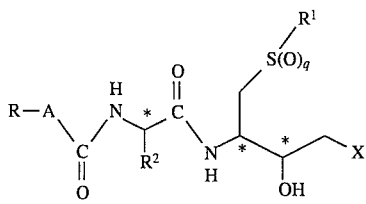

As a consequence of these asymmetric centers, the compounds of the present invention can occur as mixtures of diastereomters, racemic mixtures and as individual enantiomers. All asymmetric forms, individual isomers and combinations thereof, are within the scope invention.

As mentioned above, the invention includes the pharmaceutically acceptable salts of the compounds defined by formula I. Although generally neutral, a compound of this invention can posses a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutical acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromo acid, hydroiodic acid, sulfuric acid, phosphoric acid and the like; and organic acids such as p-tolunesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

R is aryl or unsaturated heterocycle;
A is a bond;
$R^1$ is aryl;
q is 0;
$R^2$ is $-CH_2-C(O)NH_2$, $-CH(CH_3)_2$ or $-CH_2-C(O)-NR^6-A-R^{2a}$;
X is

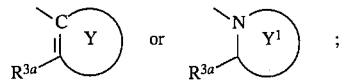

$R^{3a}$ is $-C(O)-NR^4R^4$ is independently and at each occurrence hydrogen or $C_1-C_6$ alkyl;
or a pharmaceutically acceptable salt thereof.

Of these compounds, more preferred compounds are those compounds of formula I where:

R is naphthyl, quinolinyl or quinoxalinyl each of said radicals unsubstituted or substituted with one or two substituents selected from the following group: hydrogen, halo, $C_1-C_4$ alkyl or halo($C_1-C_4$)alkyl;
Y is phenyl;
$Y^1$ is decahydro-(4aS, 8aS)-isoquinolinyl;
$R^1$ is phenyl or naphth-2-yl;
$R^2$ is $-CH_2-C(O)NH_2$; and $R^{3a}$ is —C(O)—NH(t-butyl);
or a pharmaceutically acceptable salt thereof.

Of these compounds, even more preferred compounds are those compounds where:

$R^1$ is phenyl; and

R is quinolinyl, unsubstituted or substituted with one or two substituents selected from the following group; hydrogen, halo, $C_1$–$C_4$ alkyl or halo($C_1$–$C_4$)alkyl;

or a pharmaceutically acceptable salt thereof.

The most preferred compounds are:

[1S-1R*,4S*,5S*)]-N-[1-(2'-amino-2'-oxoethyl) -2-oxo-3-aza-4-naphth-2-ylthiomethyl-5-hydroxy-6-(2"-(1"'-N (t-butyl)amino-1"'-oxomethyl)phenyl)]hexyl quinolin-2-ylcarboxamide;

[2'R-(2'R,3'R*,6'S*)]-N(t-butyl)-2-[2'-hydroxy-3'-naphth -2-ylthiomethyl-4'-aza-5',8'-dioxo-6'-(N-(benzyloxycarbonyl) amino-8'-amino]octyl benzamide;

[1S-(1R*,4R*,5S*)]-N-[1-(2'-amino-2'-oxoethyl)-2-oxo -3-aza-4-phenylthiomethyl-5-hydroxy-6-(2"-(1"'-N (t-butyl)amino-1"'-oxomethyl)phenyl)]hexyl quinolin-2-ylcarboxyamide;

[2R-(2R*,3R*,3'S*,4a'S*,8a'S*)]-N(t-butyl) -2'-[2-hydroxy-3-naphth-2-ylthiomethyl-4,7-diaza-5,8-dioxo-6 -(2"-amino-2"-oxoethyl)-8-quinolin-2yl]octyl decahydroisoquinoline-3'-carboxamide; and

[2R-(2R*,3R*,3'S*,4a'S*,8a'S*)]-N (t-butyl)-2'-[2-hydroxy-3-phenylthiomethyl-4,7-diaza-5,8-dioxo-6 -(2"-amino-2"-oxoethyl)-8-quinolin-2-yl]octyl decahydroisoquinoline-3'-carboxamide;

or a pharmaceutically acceptable salt thereof.

The following list of compounds is provided to further illustrate compounds of formula I included within the scope of the invention.

[1S-(1R*,4S*,5S*)]-N-[1-(2'-isopropyl)-2-oxo-3-aza-4-naphth-2 -ylthiomethyl-5-hydroxy-6-(2"-(1"'-N(t-butyl) amino-1"'-oxomethyl)phenyl)]hexyl quinolin-2-ylcarboxamide;

[1S-(1R*,4S*,5S*)]-N-[1-(2'-amino-2'-oxoethyl) -2-oxo-3-aza-4-naphth-2 -ylthiomethyl-5-hydroxy-6-(2"-(1"'-N(t-butyl) amino-1"'-oxomethyl)phenyl)]hexyl naphth-2-ylcarboxamide;

[1S-(1R*,4S*,5S*)]-N-[1-(2'-amino-2'-oxoethyl) -2-oxo-3-aza-4-naphth-2-ylthiomethyl-5-hydroxy-6-(2"-(1"'-N (t-butyl)amino-1"'-oxomethyl)phenyl)]hexyl quinoxolin-2-ylcarboxamide;

[1S-(1R*,4S*,5S*)]-N-[1-(2'-amino-2'-oxoethyl) -2-oxo-3-aza-4-naphth-2-ylthiomethyl-5-hydroxy-6-(2"-(1"'-N (t-butyl)amino-1"'-oxomethyl)phenyl)]hexyl 8"'-methylquinolin-2-ylcarboxamide;

[1S-(1R*,4S*,5S*)]-N-[1-(2'-amino-2'-oxoethyl) -2-oxo-3-aza-4-naphth-2-ylthiomethyl-5-hydroxy-6-(2"-(1"'-N (t-butyl)amino-1"'-oxomethyl)phenyl)]hexyl 6""-methylquinolin-2-ylcarboxamide;

[1S-(1R*,4S*,5S*)]-N-[1-(2'-amino-2'-oxoethyl) -2-oxo-3-aza-4-naphth-2-ylthiomethyl-5-hydroxy-6-(2"-(1"'-N (t-butyl)amino-1"'-oxomethyl)phenyl)]hexyl 4""-chloroquinolin-2-ylcarboxamide;

[1S-(1R*,4S*,5S*)]-N-[1-(2'-imidazol-1-ylmethyl) -2-oxo-3-aza-4-naphth-2-ylthiomethyl-5-hydroxy-6-(2"-(1"'-N (t-butyl)amino-1"'-oxomethyl)phenyl)]hexyl quinolin-2-ylcarboxamide;

[1S-(1R*,4S*,5S*)]-N-[1-(2'-imidazol-1-ylmethyl) -2-oxo-3-aza-4-naphth-2-ylthiomethyl-5-hydroxy-6-(2"-(1"'-N (t-butyl)amino-1"'-oxomethyl)phenyl)]hexyl indol-3-ylcarboxamide;

[1S-(1R*,4S*,5S*)]-N-[1-(2'-imidazol-1-ylmethyl) -2-oxo-3-aza-4-naphth-2-ylthiomethyl-5-hydroxy-6-(2"-(1"'-N (t-butyl)amino-1"'-oxomethyl)phenyl)]hexyl benzothien-3-ylcarboxamide;

[1S-(1R*,4S*,5S*)]-N-[1-(2'-methyl)-2-oxo-3-aza -4-naphth-2-ylthiomethyl-5-hydroxy-6-(2"-(1"'-(t-butyl) amino-1"'-oxomethyl)phenyl)]hexyl quinolin-2-ylcarboxamide;

[2'R-(2'R*,3'R*,6'S*)]-N(t-butyl)-2-[2'-hydroxy-3' -phenylthiomethyl-4'-aza-5',8'-dioxo-6'-(N-(benzyloxycarbonyl) amino-8'-amino]octyl benzamide;

[2'R-(2'R*,3'R*,6'S*)]-N(t-butyl)-2-[2'-hydroxy-3' -naphth-1-ylthiomethyl-4'-aza-5',8'-dioxo-6'-(N-(benzyloxycarbonyl) amino-8'-amino]octyl benzamide;

[2'R-(2'R*,3'R*,6'S*)]-N(t-butyl)-2-[2'-hydroxy-3' -naphth-2-ylthiomethyl-4'-aza-5'-oxo-6'-(N-(benzyloxycarbonyl) amino]octyl benzamide;

[2'R-(2'R*,3'R*,6'S*)]-N(t-butyl)-2-[2'-hydroxy-3' -naphth-2-ylthiomethyl-4'-aza-5'-6'-(N-(phenylethoxycarbonyl) amino]8'-amino]octyl benzamide;

[2'R-(2'R*,3'R*,6'S*)]-N(t-butyl)-2-[2'-hydroxy-3' -naphth-2-ylthiomethyl-4'-aza-5',9'-dioxo-6'-(N-(benzyloxycarbonyl) amino-9-amino]nonyl benzamide;

[2'R-(2'R*,3'R*,6'S*)]-N(t-butyl)-2-[2'-hydroxy-3' -naphth-2-ylthiomethyl-4'-aza-5',9'-dioxo-6'-(N-(benzyloxycarbonyl) amino-9-hydroxy]nonyl benzamide;

[2'R-(2'R*,3'R*,6'S*)]-N(t-butyl)-2-[2'-hydroxy-3' -phenylthiomethyl-4'-aza-5',9'-dioxo-6'-(N-(benzyloxycarbonyl) amino-9-amino]nonyl benzamide;

[2'R-(2'R*,3'R*,6'S*)]-N(t-butyl)-2-[2'-hydroxy-3' -naphth-2-ylthiomethyl-4'-aza-5'-oxo-6'-(N-(benzyloxycarbonyl) amino-7'-phenyl]heptyl benzamide;

[2'R-(2'R*,3'R*,6'S*)]-N(t-butyl)-2-[2'-hydroxy-3' -naphth-2-ylthiomethyl-4'-aza-5'-oxo-6'-(N-(benzyloxycarbonyl) amino-7'-thienyl]heptyl benzamide;

[2'R-(2'R*,3'R*,6'S*)]-N(t-butyl)-2-[2'-hydroxy-3' -naphth-2-ylthiomethyl-4'-aza-5'-oxo-6'-(N-(benzyloxycarbonyl) amino-7'-furyl]heptyl benzamide;

[1S-(1R*,4S*,5S*)]-N-[1-(2'-amino-2'-oxoethyl) -2-oxo-3-aza-4-phenylthiomethyl-5-hydroxy-6-(2"-(1"'-(N(t-butyl) amino-1"'-oxomethyl)phenyl)]hexyl quinoxolin-2-ylcarboxamide;

[1S-(1R*,4S*,5S*)]-N-[1-(2'-amino-2'-oxoethyl) -2-oxo-3-aza-4-phenylthiomethyl-5-hydroxy-6-(2"-(1"'-(N(t-butyl) amino-1"'-oxomethyl)phenyl)]hexyl naphth-2-ylcarboxamide;

[1S-(1R*,4S*,5S*)]-N-[(1-(2'-amino-2'-oxoethyl) -2-oxo-3-aza-4-phenylthiomethyl-5-hydroxy-6-(2"-(1"'-N (t-butyl)amino-1"'-oxomethyl)phenyl)]hexyl isoquinolin-2-ylcarboxamide;

[1S-(1R*,4S*,5S*)]-N-[(1-(2'-amino-2'-oxoethyl) -2-oxo-3-aza-4-phenylthiomethyl-5-hydroxy-6-(2"-(1"'-N (t-butyl)amino-1"'-oxomethyl)phenyl)]hexyl 6"'-methylquinolin-2-ylcarboxamide;

[1S-(1R*,4S*,5S*)]-N-[(1-(2'-amino-2'-oxoethyl) -2-oxo-3-aza-4-phenylthiomethyl-5-hydroxy-6-(2"-(1"'-N (t-butyl)amino-1"'-oxomethyl)phenyl)]hexyl 8"'-chloroquinolin-2-ylcarboxamide;

[1S-(1R*,4S*,5S*)]-N-[(1-(isopropyl)-2-oxo-3-aza -4-phenylthiomethyl-5-hydroxy-6-(2"-(1"'-N (t-butyl)amino-1"'-oxomethyl)phenyl)]hexyl quinolin-2-ylcarboxamide;

[1S-(1R*,4S*,5S*)]-N-[(1-(3'-amino-3'-oxoethyl) -2-oxo-3-aza-4-phenylthiomethyl-5-hydroxy-6-(2'-(1"'-N (t-butyl)amino-1"'-oxomethyl)phenyl)]hexyl quinolin-2-ylcarboxamide;

[1S-(1R*,4S*,5S*)]-N-[1-furylmethyl-2-oxo-3-aza-4-phenylthiomethyl -5-hydroxy-6-(2"-(1"'-N(t-butyl)amino-1"'-oxomethyl)phenyl)] hexyl quinolin-2-ylcarboxamide;

[1S-(1R*,4S*,5S*)]-N-[1-(2'-amino-2'-oxoethyl) -2-oxo-3-aza-4-phenylthiomethyl-5-hydroxy-6-(2"-(1"'-N (t-butyl)amino-1"'-oxomethyl)phenyl)]hexyl benzothien-2-ylcarboxamide;

[2R-(2R*,3R*, 3'S*, 4a'S*,8a'S*)]-N(t-butyl) -2'-[2-hydroxy-3-naphthyl-2-ylthiomethyl-4,7-diaza-5,8-dioxo-6-(2"-amino -2"-oxoethyl)-8-quinoxolin-2-yl]octyl-2-decahydroisoquinoline-3'-carboxamide;

[2R-(2R*,3R*, 3'S*, 4a'S*,8a'S*)]-N(t-butyl) -2'-[2-hydroxy-3-naphthyl-1-ylthiomethyl-4,7-diaza-5,8-dioxo-6-isopropyl -8-quinolin-2-yl]octyl-2-decahydroisoquinoline-3'-carboxamide;

[2R-(2R*,3R*,3'S*,4a'S*,8a'S*)]-N(t-butyl) -2'-[2-hydroxy-3-naphth-2-ylthiomethyl-4,7-diaza-5,8-dioxo-6-(2"-amino-2"-oxoethyl)-8-benzothien-2-yl]octyl decahydroisoquinoline-3'-carboxamide;

[2R-(2R*,3R*,3'S*,4a'S*,8a'S*)]-N(t-butyl) -2'-[2-hydroxy-3-naphth-2-ylthiomethyl-4,7-diaza-5,8-dioxo-6-isopropyl-8-quinolin-2-yl]octyl decahydroisoquinoline-3'-carboxamide;

[2R-(2R*,3R*,3'S*,4a'S*,8a'S*)]-N(t-butyl) -2'-[2-hydroxy-3-naphth-2-ylthiomethyl-4,7-diaza-5,8-dioxo-6 -(imidazol-4-ylmethyl)-8-quinolin-2-yl]octyl decahydroisoquinoline-3'-carboxamide;

[2R-(2R*,3R*,3'S*,4a'S*,8a'S*)]-N(t-butyl) -2'-[2-hydroxy-3-naphth-2-ylthiomethyl-4,7-diaza-5,8-dioxo-6 -(2"-amino-2"-oxoethyl)-8-naphth-2-yl]octyl decahydroisoquinoline-3'-carboxamide;

[2R-(2R*,3R*,3'S*,4a'S*,8a'S*)]-N(t-butyl) -2'-[2-hydroxy-3-naphth-2-ylthiomethyl-4,7-diaza-5,8-dioxo-6 -(2", 2"-dimethylethyl)-8-quinolin-2-yl]octyl decahydroisoquinoline-3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -(2"-amino-2"-oxoethyl)-8-quinolin-8-yl]octyl decahydroisoquinoline -3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -(2"-amino-2"-oxoethyl)-8-isoquinolin-1-yl]octyl decahydroisoquinoline -3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -methyl-8-quinolin-2yl]octyl decahydroisoquinoline-3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -(2"-amino-2"-oxoethyl)-8-naphth-1-yl]octyl decahydroisoquinoline-3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -(2"-amino-2"-oxoethyl)-8-(6"'-methylquinolin-2-yl)]octyl decahydroisoquinoline-3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -(2"-amino-2"-oxoethyl)-8-(4"'-chloronaphth-2yl)octyl decahydroisoquinoline-3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -(2"-amino-2"-oxoethyl)-8-benzimidazol-2-yl]octyl decahydroisoquinoline-3'-carboxamide;

[2R-(2R*,3R*,3'S*,4a'S*,8a'S*)]-N(t-butyl) -2'-[2-hydroxy-3-phenylthiomethyl-4,7-diaza-5,8-dioxo-6 -(2"-amino-2"-oxoethyl)-8-benzofur-2-yl]octyl decahydroisoquinoline-3'-carboxamide;

The compounds of the present invention can be prepared according to the procedures shown below in Reaction Scheme I.

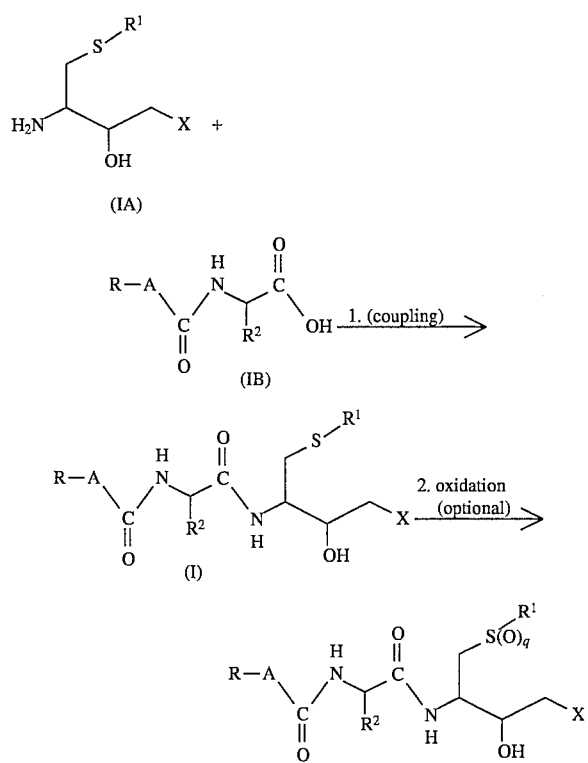

Reaction Scheme I where:

q is 1 or 2; and

R, A, $R^2$, $R^1$ and X are as defined above for formula I.

Reaction Scheme I, above, is accomplished by carrying out the above chemical reactions in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction I.1 is a standard coupling reaction commonly employed in the synthesis of peptides which is carried out by reacting a appropriately substituted amine of formula IA, with an appropriately substituted carboxylic acid reactant of formula IB, in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran and dimethylformamide, preferably a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl)phosphinic chloride (BOS-Cl) or N-ethoxycarbonyl-2-ethoxy-1,2-dihydroquinoline (EEDQ). A preferred coupling reagent for this reaction is DCC. A promoting agent is preferably included in this reaction; a preferred promoting agent is hydroxybenzotriazole hydrate (HOBT·H₂O).

In reaction I.2, the compound prepared in reaction I.1 is oxidized using using standard procedures known in the art. For example, the compound prepared in reaction I.1 is combined with an oxidizing agent in an organic or aqueous solvent at a temperature from about −78° C. to about 50° C. Typical oxidizing agents include hydrogen peroxide, sodium iodate, potassium permanganate, osmium tetraoxide and peracids such as peracetic acid or meta-chloroperbenzoic acid. Typical solvents include water or a halocarbon, such as methylene chloride or chloroform. Solvent choice is not critical so long as the solvent employed is inert to the ongoing reaction and the reactants are sufficiently solubilized to effect the desired reaction. The reaction is preferably carried out in methylene chloride at a temperature from about −25° C. to about 25° C. A preferred oxidizing agent is meta-chloroperbenzoic acid.

The compounds of the formula IA are useful, as described above, for making the compounds of formula I. Compounds of formula IA where X is a group having the formula

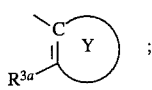

can be prepared according to the procedures shown below in Reaction Scheme A.

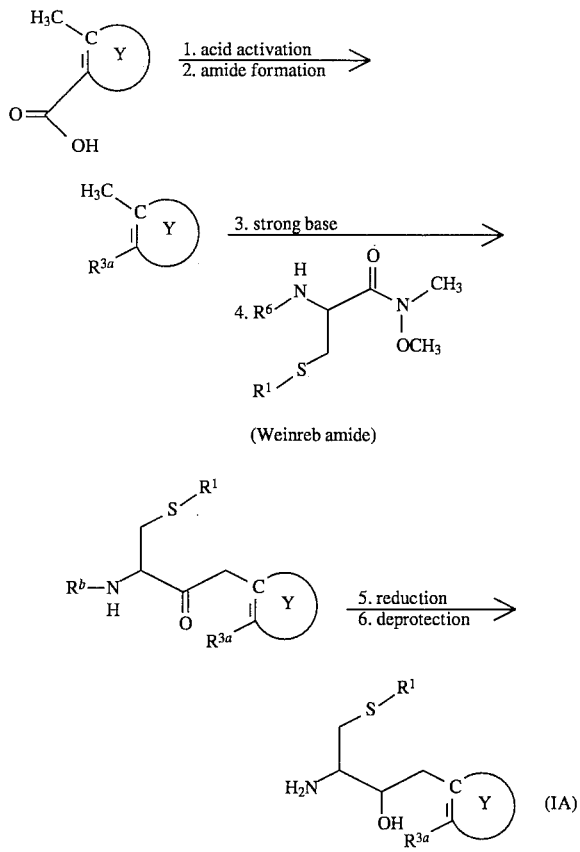

where:

$R^b$ is an amino-protecting group; and $R^1$, $R^{3a}$ and Y are as defined above.

Reaction Scheme A, above, is accomplished by carrying out the above reactions 1–6 in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction A.1, the reaction is carried out by activating, that is, converting, a suitably substituted aryl, heterocycle or unsaturated heterocycle carboxylic acid to the corresponding acyl chloride or acyl bromide by reaction with thionyl chloride, thionyl bromide, phosphorous trichloride, phosphorous tribromide, phosphorous pentabromide or phosphorous pentachloride according to procedures and under conditions known in the art. Suitable aryl, heterocycle or unsaturated heterocycle carboxylic acid compounds are commercially available or prepared by procedures known in the art.

In Reaction A.2, the acyl chloride or acyl bromide, prepared in Reaction A.1, is reacted with ammonia or a primary or secondary amine having the structure:

$$H-NR^4R^4,$$

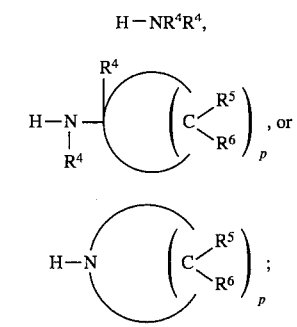

where $R^4$, $R^5$, $R^6$ and p are as defined above for formula I, in a nonpolar aprotic solvent or mixture of solvents in the presence or absence of an acid scavenger to afford the corresponding amine. The reaction is carried out at a temperature of from about −20° C. to about 25° C. Typical solvents for this reaction include ethers and chlorinated hydrocarbons, preferably diethyl ether, chloroform or methylene chloride. Preferably, this reaction is carried out in the presence of an acid scavenger such as a tertiary amine, preferably triethylamine.

In Reaction A.3, the amine prepared in Reaction A.2, is reacted with a strong base in the presence of a solubilizing agent to afford the corresponding anion which is then reacted in Reaction A.4 with a Weinreb amine to afford a ketone. Reaction A.3 is carried out in an aprotic solvent at a temperature of from about −78° C. to about 0° C. Typical bases used in Reaction A.3 include lithium amide bases and alkyl lithium bases, preferably $C_1$–$C_4$ alkyllithium bases and lithium di($C_1$–$C_4$)alkylamide bases. Typical solubilizing agents for Reaction A.3 are tetramethyl($C_1$–$C_4$)alkylenediamines, preferably tetramethylethylenediamine. Reaction A.4 is carried out in an aprotic solvent at a temperature from about −80° C. to about −40° C. Typical solvents for Reactions A.3 and A.4 include ethers, preferably tetrahydrofuran. In Reaction A.4, the anion is generally employed in an amount ranging from about equimolar proportions to about a three molar excess of the anion, preferably in about a two molar excess of the anion relative to the Weinreb amide reactant.

In Reaction A.5, the ketone prepared in Reaction A.3 is reduced by the corresponding alcohol using a suitable reducing agent. The reaction is carried out in a protic solvent at a temperature of from about −25° C. to about 25° C. Typical reducing agents for this reaction include sodium borohydride, lithium borohydride, diisobutylaluminum hydride, and sodium bis(2-methoxyethoxy)aluminum hydride. A preferred reducing agent is sodium borohydride. Typical protic solvents for this reaction include alcohols, preferably ethanol.

Reaction A.6 is a standard amino deprotection reaction using procedures and methods known in the art to afford the corresponding amine of formula IA. This amine is then reacted according to the procedure detailed above in Reaction Scheme I. This amine may be reacted without purification, but it is preferably purified first.

The compounds of formula IA where X is a group having the structure

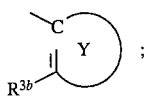

are prepared according to the procedure shown below in Reaction Scheme B.

Reaction Scheme B

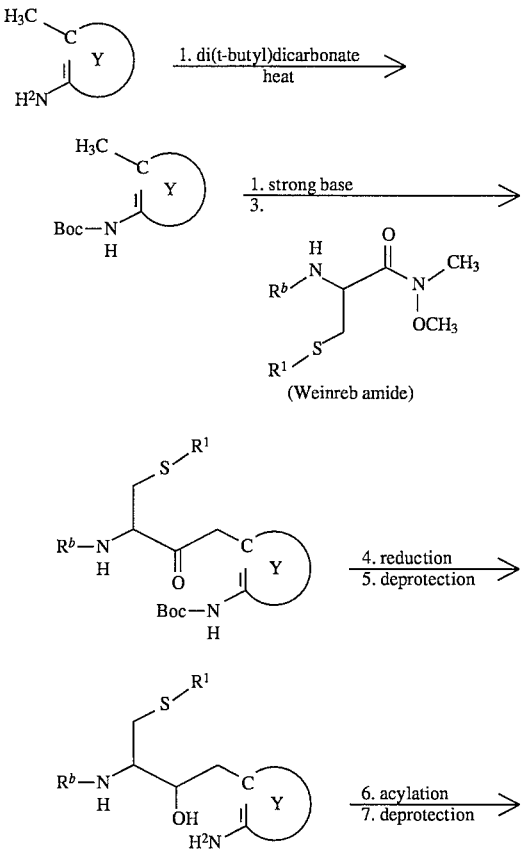

-continued
Reaction Scheme B

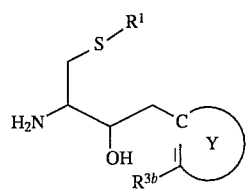

where $R^b$, $R^1$, Y and $R^{3b}$ are as defined above.

Reaction Scheme B, above, is accomplished by carrying out reactions 1–7 in sequential order. Once a reaction is complete, the intermediate compound may be isolated by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction B.1, a suitably substituted aryl or unsaturated heterocycle amine is protected, under standard conditions used with amino-protecting groups known in the art. Reactions B.2 through B.5 are carried out substantially as described above in Reaction Scheme A.3–A.6 with the exception that in Reaction Scheme B, an additional deprotection reaction, Reaction B.5, is necessary to remove the amino-protecting group introduced in Reaction B.1. This is a standard amino deprotection reaction using procedures and methods known in the art. For example, the t-Boc group illustrated in Reaction Scheme II.1 may be removed using a strong acid, preferably trifluoroacetic acid.

In Reaction Scheme B.6, the illustrated intermediate is acylated with a suitable acyl halide, isocyanate or chloroformate, preferably in the presence of an acid scavenger such as a tertiary amine, preferably triethyl amine. The reaction is carried out at a temperature of from about −20° C. to about 25° C. Typical solvents for this reaction include ethers and chlorinated hydrocarbons, preferably diethyl ether, chloroform or methylene chloride.

Reaction B.7 is a standard amino deprotection reaction using procedures and methods known in the art to afford the corresponding amine IA, which is used in Reaction Scheme I, above. This amine may be reacted without purification, but it is preferably purified first.

The compounds of formula I where X is a group having the structure:

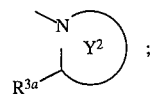

are prepared according to the procedures shown below in Reaction Scheme C.

Reaction Scheme C

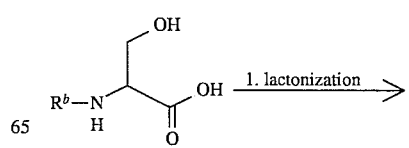

-continued
Reaction Scheme C

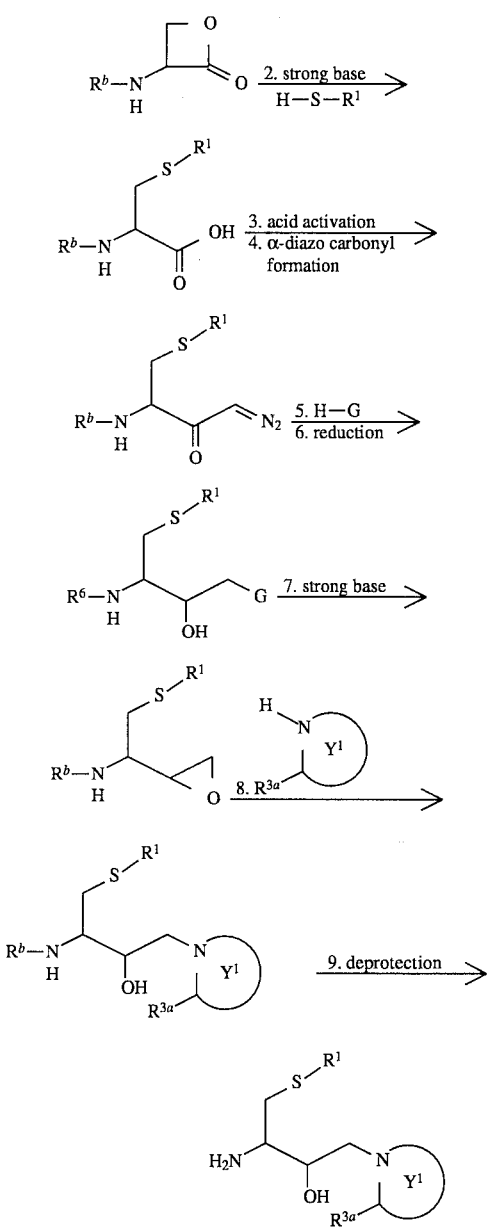

where:

$R^1$, $Y^1$, $R^{3a}$ and $R^b$ are as defined above; and

G is halo.

Reaction Scheme C, above, is accomplished by carrying out reactions 1–9 in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction C.1, a β-lactone is formed by reacting amino-protected serine with triphenylphosphine and diethylazodicarboxylate (DEAD) in an aprotic solvent at a temperature of from about −80° C. to 0° C. The reaction is preferably carried out in an ether, such as tetrahydrofuran at a temperature of from about −80° C. to −50° C.

In Reaction Scheme C.2, the lactone ring prepared in reaction C.1 is opened by reacting the lactone with an appropriately substituted thioanion having the structure, —S—$R^1$, where $R^1$ is as defined above for formula I. The thionanion compound is preferably formed by reacting the corresponding thiol with a strong base, such as sodium hydride or potassium hydride. The reaction is typically carried out in an aprotic solvent at a temperature from about 0° C. to about 40° C. and under an inert atmosphere, such as nitrogen. Typical solvents for this reaction include ethers, preferably tetrahydrofuran.

Reaction C.3 is carried out by activating, that is, converting, a suitably substituted compound prepared in Reaction C.2 to the corresponding mixed anhydride under conditions known in the art. For example, the compound of formula from Reaction C.2 can be reacted with an $C_1$-$C_6$ alkylchloroformate or benzylchloroformate, preferably in the presence of an acid scavenger. Preferred acid scavengers are the trialkylamines, preferably triethylamine. A preferred alkylchloroformate reactant is isobutylchloroformate. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction C.4 without further isolation or purification.

Reaction C.4 is accomplished in two steps. First, a solution of sodium hydroxide, covered with a layer of an ether solvent, preferably diethyl ether, is reacted with a large excess of N-methyl-N-nitro-N-nitrosoguanidine to from a diazomethane reactant. The sodium hydroxide is preferably used as an aqueous solution having about four to six mol/liter of sodium hydroxide. Once this reaction is substantially complete, the organic layer is dried over a dessicant such as potassium hydroxide. This solution is then reacted with the mixed anhydride from Reaction C.3, above to from the corresponding α-diazo carbonyl compound. The diazomethane reactant is preferably used in this reaction without isolation or purification. The reaction is typically carried out at a temperature of from about −50° C. to about −30° C., preferably about −30° C.

In Reaction C.5, the α-diazo carbonyl compound prepared in Reaction C.4 is reacted with an acid of the formula H—G where G is halo, in an aprotic solvent such as diethyl ether to form an α-halo carbonyl compound. A preferred acid reactant is hydrochloric acid which results in the α-chloro carbonyl compound. The reaction is typically carried out at a temperature from about −30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by thin layer chromatography.

In Reaction C.6, the carbonyl moiety on the compound prepared in Reaction C.5 is reduced using standard conditions known in the art to form the α-chloro hydroxy compound. For example, the compound prepared in Reaction C.5 is combined with a reducing agent in a mixture of solvents. Typical reducing agents include sodium borohydride, lithium borohydride, zinc borohydride, diisobutylaluminum hydride or sodium bis(2-methoxyethyoxy)aluminum hydride. A preferred reducing agent is sodium borohydride.

Typical solvent mixtures include a protic and aprotic mixture such as tetrahydrofuran/water. Solvent choice is not critical so long as the solvent employed is inert to the ongoing reaction and the reactants are sufficiently solubilized to effect the desired reaction. The reaction is typically carried out at a temperature from about −10° C. to about 10° C., preferably about 0° C.

In Reaction C.7, the α-chloro hydroxy compound prepared in Reaction C.6 is treated with a strong base to form the corresponding epoxide under standard conditions known in the art. For example, the α-chloride hydroxy compound may be reacted with a potassium hydroxide/ethanol mixture in an organic solvent such as ethyl acetate. Solvent choice is not critical so long as the solvent employed is inert to the ongoing reaction and the reactants are sufficiently solubilized to effect the desired reaction. The reaction is typically carried out at a temperature from about 0° C. to about the reflux temperature of the solvent. Preferably the reaction is carried out at room temperature.

In Reaction C.8, the epoxide prepared in Reaction C.7 is reacted with a heterocyclic reactant of the formula

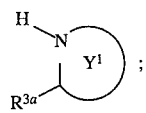

in a protic solvent at a temperature of from about 70° C. to 100° C. Solvent choice is not critical so long as the solvent employed is inert to the ongoing reaction and the reactants are sufficiently solubilized to effect the desired reaction. Typical solvents for this reaction include the alcohols, preferably ethanol. The reaction is preferably carried out at a temperature of about 80° C.

Reaction C.9 is a standard amino deprotection reaction using procedures and methods known in the art to afford the corresponding amine, IA, which may be used in Reaction I, above.

The heterocycle reactants, used in Reaction C.8 above, of the formula

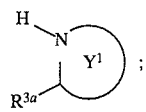

can be prepared using procedures and methods known in the art. For example, the heterocyclic reactants were typically prepared from the corresponding amino-protected amino acids by acid activation followed by treatment with an alkylamine. This reaction is typically carried out in the presence of an acid scavenger, such as N-methyl-morpholine. Removal of the amino-protecting group using standard chemical deprotecting techniques provides the heterocyclic reactants used above in Reaction C.8. Specifically, the [3S-(3R*,4aR*,8aR*)]-decahydroisoquinoline-3-N-t-butyoxycarboxamide was prepared using (2S)-1,2,3,4-tetrahydro-3-isoquinolinecarboxylic acid by the following procedure:

1) amino-protection (t-Boc);
2) acid activation/reaction with t-butylamine;
3) catalytic hydrogenation
4) amino-deprotection The Weinreb amide used as a reactant is Reaction A.4 and B.3 can be prepared by reacting the compound prepared in Reaction scheme C.2 above with N-methoxy-N-methylamine in the presence of a promoting agent, an acid scavenger, and a coupling agent in an aprotic solvent or mixture of solvents at a temperature of from about −25° C. to 25° C. A preferred promoting agent for this reaction is $HOBT \cdot H_2O$. Preferred acid scavengers are tertiary alkylamines, preferably triethylamine and N-methyl-morpholine. A preferred coupling reagent is ethyl dimethylaminopropylcarbodiimide hydrochloride. The Weinreb amine afforded by this reaction is preferably isolated prior to its use in Reactions A.4 and B.3.

The carboxylic acid reactants used in the coupling reaction described in Reaction I.1, to the extent not commercially available, are prepared using procedures known in the art.

It will be understood by those skilled in the art that in performing the processes described above it may be desirable to introduce chemical protecting groups into the reactants in order to prevent secondary reactions from taking place. Any amine, alkylamine or carboxy groups which may be present on the reactants may be protected using any standard amino- or carboxy-protecting group which does not adversely affect the remainder of the molecule's ability to react in the manner desired. The various protective groups may then be removed simultaneously or successively using methods known in the art.

As noted above, all asymmetric forms, individual isomers and combinations thereof are considered part of this invention. Such isomers may be prepared from their respective precursors by the procedures described above, or by resolving the racemic mixtures. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

The compounds employed as initial starting material in the synthesis of the compounds of this invention are known and, to the extent not commercially available are readily synthesized by standard procedure commonly employed in the art.

The pharmaceutically acceptable salts of the invention are typically formed by reacting a compound of formula I with an equimolar or excess amount of acid or base. The reactants are generally combined in a mutual solvent such as diethyl ether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS (FD)", "MS(FAB)", "IR", "UV", "Analysis", "HPLC", and "TLC", respectively. In addition, the absorption maxima listed for the IR spectra are only those of interest and not all of the maximum observed.

In conjunction with the NMR spectra, the following abbreviations are used: "s" is singlet, "d" is doublet", "dd"

is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Brüker Corp. 270 MHz instrument or on a General Electric QE-300 300 MHz instrument. The chemical shifts are expressed in delta (δ) values (parts per million downfield form tetramethylsilane). MS(FD) were taken on a Varian-MAT 731 Spectrometer using carbon dendrite emitters. EIMS were obtained on a CEC 21-110 instrument from Consolidated Electrodynamics Corporation. MS(FAB) spectra were obtained on a VG ZAB-3 spectrometer. IR spectra were obtained on a Perkin-Elmer 281 instrument. UV spectra were obtained on a Cary 118 instrument. TLC was carried out on E. Merck silica gel plates. Melting points are uncorrected.

Preparation 1

A. (2R)-2-N(t-Butoxycarbonyl)amino-3-naphth-2-ylthio propanoic acid

To a solution of 2.14 g (13.4 mmol) 2-naphthalene diol in 40 mL of anhydrous tetrahydrofuran at room temperature, was added a suspension of 0.54 g (13.5 mmol) of sodium hydride in mineral oil. After approximately 15 minutes, a solution of 2.5 g (13.4 mmol) of (S)-N(t-butoxycarbonyl)-serine-β-lactone in 30 mL of tetrahydrofuran was added dropwise. The resultant reaction mixture was allowed to react for approximately one hour and then was concentrated under reduced pressure to provide a gummy solid. This solid was purified using flash chromatography (eluent of 1% methanol in ethyl acetate) to provide 4.35 g of a white solid.

Yield: 94%.

$^1$H NMR (CDCl$_3$): δ 10.25 (s, 1H), 7.89 (s, 1H), 7.78 (m, 3H), 7.46 (m, 3H), 5.39 (d, 1H), 4.61 (m, 1H), 3.49 (m, 2H), 1.37 (s, 9H).

B. 2R)-N(Methoxy-N(methyl) [2-N(t-butoxycarbonyl)amino-3-naphth-2-ylthio]propanamide To a cold (0° C.) solution containing 4.3 g (12.4 mmol) of the subtitled intermediate of Preparation 1A, 1.58 g (16.15 mmol) of N,O-dimethylhydroxylamine hydrochloride, 2.18 g (16.15 mmol) of 1-hydroxybenzotriazole hydrate (HOBT·H$_2$O), 2.24 mL (16.15 mmol) of triethylamine and 2.73 mL (24.86 mmol) N-methylmorpholine in 100 mL of methylene chloride, was added 2.62 g (13.67 mmol) of 1-(3-dimethylaminopropyl) -3-ethylcarbodiimide hydrochloride (EDC). The resulting reaction mixture was allowed to react at room temperature overnight. The reaction mixture was diluted with 100 mL of hexane, washed sequentially with 200 mL of a saturated sodium bicarbonate solution and 200 mL of brine. The resulting layers were separated and the organic layer was dried over sodium sulfate, filtered and then concentrated under reduced pressure to provide a clear yellow oil.

$^1$H NMR (CDCl$_3$): δ 7.90 (s, 1H), 7.80 (m, 3H), 7.49 (m, 3H), 5.41 (d, 1H), 4.92 (m, 1H), 3.59 (s, 3H), 3.18–3.46 (m, 2H), 3.05 (s, 3H), 1.42 (s, 9H).

MS (FD): m/e 391 (M$^+$), 390 (100).

C. (3R)-N(t-Butyl)-2-[2'-oxo-3'-N(t-butoxycarbonyl)amino-4'-naphth -2-ylthio]butyl benzamide To a cold (−78° C.) solution containing 8.60 (45 mmol) of N(t-butyl)-2-methylbenzamide and 14.2 mL (95 mmol) of N,N,N',N'-tetramethylethylenediamine in 100 mL of anhydrous tetrahydrofuran and under an inert atmosphere, was slowly added 111 mL (95 mmol) of a 0.85M solution of sec-butyllithium in hexanes, via syringe. The internal temperature of the reaction vessel was monitored during the addition of the sec-butyllithium to ensure that the temperature did not exceed −57° C. After allowing the resultant reaction mixture to react for approximately one hour at −78° C., a solution of 7.90 g (20 mmol) of the subtitled intermediate of Preparation 1B in 80 mL of tetrahydrofuran was added dropwise. When the addition was complete, the reaction was warmed to −20° C. and then was quenched by the addition of a saturated ammonium chloride solution. The resulting mixture was then diluted with 600 mL of diethyl ether. The resulting layers were separated and the organic layer was washed sequentially with a 1M sodium bisulfate solution and a brine solution, dried over sodium sulfate, filtered and then concentrated under reduced pressure to provide a yellow oil. This oil was purified using flash chromatography (gradient eluent of 10–50% ethyl acetate in hexane) to provide 8.5 g of the desired subtitled intermediate.

Yield: (82%).

$^1$H NMR (CDCl$_3$): δ 7.90 (s, 1H), 7.79 (t, 3H), 7.48 (m, 3H), 7.40 (d, 1H), 7.29 (m, 2H), 7.05 (d, 1H), 5.94 (br.s, 1H), 5.65 (m, 1H), 4.65 (d, 1H), 4.24 (d, J=17 Hz, 1H), 3.86 (d, J=17 Hz, 1H), 3.66 (m, 1H), 3.40 (m, 1H), 1.42 (s, 9H), 1.39 (s, 9H).

MS (FD): m/e 521 (M$^+$), 521 (100).

D. [(2R-(2R*,3R*)]-N(t-Butyl)-2-[2'-hydroxy-3'-N (t-butyoxycarbonyl)amino-4'-naphth-2-ylthio]butyl benzamide To a solution of 3.49 g (6.7 mmol) of the subtitled intermediate of Preparation 1C in 150 mL of absolute ethanol, was added 0.51 (13 mmol) of sodium borohydride and the resulting reaction mixture was allowed to react overnight at room temperature. The reaction was then cooled to 0° C., quenched with a saturated ammonium chloride solution and diluted with 550 mL of methylene chloride. The resulting layers were separated and the organic layer was washed sequentially with 1N hydrochloric acid, 2N sodium hydroxide and brine, dried over sodium sulfate, filtered and then concentrated under reduced pressure to provide a colorless foam. This foam was purified using flash chromatography (gradient of 10–25% hexane in ethyl acetate) to provide 2.78 g of the desired subtitled intermediate.

Yield: 78%.

$^1$H NMR (CDCl$_3$): δ 7.84 (s, 1H), 7.73 (t, 3H), 7.41 (m, 3H), 7.29 (t, 2H), 7.16 (t, 2H), 6.53 (s, 1H), 5.32 (d, 1H), 3.86 (m, 2H), 3.33 (m, 2H), 2.83 (m, 2H), 1.40 (s, 9H).

MS (FD): m/e 523 (M$^+$), 522 (100).

Analysis for C$_{30}$H$_{38}$N$_2$O$_4$S: Calcd: C, 68.94; H, 7.33; N, 5.36; Found: C, 68.65; H, 7.34; N, 5.15.

E. [(2R-(2R*,3R*)]-N(t-Butyl)-2-[2'-hydroxy-3' -amino-4'-naphth-2-ylthio]butyl benzamide To a cold (0° C.) solution of 2.89 g (5.53 mmol) of the subtitled intermediate of Preparation 1D in 100 mL of methylene chloride, was added 18 mL of trifluoroacetic acid. The resulting reaction mixture was allowed to react for approximately one hour. The reaction mixture was then concentrated under reduced pressure to provide a foam. This foam was slurried in toluene and then concentrated under reduced pressure to provide a foam which was purified using flash chromatography (eluent of 5% methanol in methylene chloride) to provide 1.71 g of a white foam.

Yield: 74%.

$^1$H NMR (CDCl$_3$): δ 7.75–7.85 (m, 4H), 7.24–7.51 (m, 7H), 6.06 (s, 1H), 3.75 (m, 1H), 3.61 (m, 1H), 3.07 (m, 2H), 2.95 (m, 2H), 1.47 (s, 9H).

MS (FD): m/e 423 (M$^+$), 422 (100).

Preparation 2

A. (2R)-2-N(t-Butoxycarbonyl)amino-3-phenylthio propanoic acid

The desired subtitled compound was prepared substantially in accordance with the procedure detailed in Preparation 1A.

Yield: 5.1 g (95%).

$^1$H NMR (CDCl$_3$): δ 7.43 (m, 2H), 7.22–7.34 (m, 3H), 5.31 (m, 1H), 4.54 (m, 1H), 3.37–3.48 (m, 2H), 1.43 (s, 9H).

MS (FD): m/e 297 (M$^+$), 297 (100).

B. (2R)-N(Methoxy)-N(methyl) [2-N(t-butoxycarbonyl)amino-3-phenylthio]propanamide The desired subtitled compound was prepared substantially in accordance with the procedure detailed in Preparation 1B.

Yield: 4.40 g (79%).

$^1$H NMR (CDCl$_3$): δ 7.33 (m, 2H), 7.17 (m, 2H), 7.09 (m, 1H), 5.53 (d, J=9 Hz, 1H), 4.73 (m, 1H), 3.45 (s, 3H), 3.19 (m, 1H), 2.95–3.06 (m, 4H), 1.33 (s, 9H).

MS (FD): m/e 341 (M$^+$), 340 (100).

C. (3R)-N(t-Butyl)-2-[2'-oxo-3'-N(t-butoxycarbonyl)amino-4'-phenylthio]butyl benzamide The desired subtitled compound was prepared substantially in accordance with the procedure detailed in Preparation 1C.

Yield: 2.20 g (58%).

$^1$H NMR (CDCl$_3$): δ 7.39 (m, 3H), 7.18–7.35 (m, 5H), 7.09 (d, J=6 Hz, 1H), 6.00 (s, 1H), 5.63 (d, J=7 Hz, 1H), 4.56 (m, 1H), 4.20 (d, J=17 Hz, 1H), 3.84 (d, J=17 Hz, 1H), 3.54 (m, 1H), 3.26 (m, 1H), 1.41 (s, 9H).

D. [(2R-(2R*,3R*)]-N(t-Butyl)-2-[2'-hydroxy-3'-N (t-butoxycarbonyl)amino-4'-phenylthio]butyl benzamide The desired subtitled compound was prepared substantially in accordance with the procedure detailed in Preparation 1D.

Yield: 1.85 (80%).

$^1$H NMR (CDCl$_3$): δ 7.17–7.45 (m, 9H), 6.04 (br.s, 1H), 5.08 (m, 1H), 3.87 (m, 2H), 3.32 (m, 2H), 2.90 (m, 3H), 1.47 (d, 18H).

MS (FD): m/e 473 (M$^+$), 472 (100).

Analysis for C$_{26}$H$_{36}$N$_2$O$_4$S: Calcd: C, 66.07; H, 7.68; N, 5.93; Found: C, 66.09; H, 7.75; N, 5.86.

E. [(2R-(2R*,3R*)]-N(t-Butyl)-2-[2'-hydroxy-3'-amino-4'-phenylthio]butyl benzamide The desired subtitled compound was prepared substantially in accordance with the procedure detailed in Preparation 1E.

Yield: 1.00 g (81%).

$^1$H NMR (CDCl$_3$): δ 7.19–7.43 (m, 9H), 6.04 (br.s, 1H), 5.43 (br.s, 1H), 3.71 (m, 1H), 3.47 (m, 1H), 2.83–3.01 (m, 4H), 1.47 (s, 9H).

MS (FD): m/e 373 (M$^+$), 372, 373 (100).

Preparation 3

A. (2R)-N(Benzyloxycarbonyl)amino-3-naphth-2-ylthio propanoic acid

To a solution of 1.28 g (8.00 mmol) of naphthalene-2-thio in 30 mL tetrahydrofuran, was slowly added 1.77 g (8.16 g) of 60% sodium hydride, under nitrogen. After stirring for approximately 15 minutes, N(benzyloxycarbonyl)serine-β-lactone in 20 mL of tetrahydrofuran was slowly added. The reaction mixture was allowed to react at room temperature for approximately one hour, and then concentrated under reduced pressure to provide a residue. This residue was dissolved in ethyl acetate and washed sequentially with 0.5N sodium bisulfate and a saturated brine solution. The resulting layers were separated and the organic layer was dried over sodium sulfate, filtered, and then concentrated under reduced pressure to provide a residue. This residue was purified using flash chromatography to provide 2.08 g of a pale yellow solid.

Yield: 68%.

H NMR (CDCl$_3$): δ 3.42–3.61 (br.m, 2H), 5.53–5.76 (br.s, 1H), 4.85–5.08 (br.m, 2H), 5.54–5.76 (br.s, 1H), 7.06–7.97 (m, 12H).

[α]$_D$ –55.72° (c 1.0, MeOH).

IR KBr): 3348, 3048, 1746, 1715, 1674, 1560, 1550, 1269, 1200, 1060 cm$^{-1}$.

MS (FD): m/e 381 (M$^+$), 381 (100).

Analysis for C$_{20}$H$_{19}$NO$_4$S: Calcd: C, 66.12; H, 5.02; N, 3.67; Found: C, 66.22; H, 5.04; N. 3.86.

E. (3R) Benzyl 2-aza-3-(naphth-2ylthiomethyl)-4-oxo-5-diazo pentanoate

To a cold (–30° C.) solution of 15.38 g (40.3 mmol) of the subtitled intermediate from Preparation 3A in 230 mL of ethyl acetate and under nitrogen, was slowly added 5.62 mL (40.3 mmol) of triethylamine, via syringe. To the resulting solution was then added 7.84 mL (60.5 mmol) of isobutyl chloroformate, via syringe. In a separate flash, 10 g of N(methyl)-N(nitro)-N(nitroso)-guanidine was carefully added to a bilayer mixture of 170 mL of diethyl ether and 170 mL of a 5N sodium hydroxide solution, resulting in a large evolution of gas. When this reaction was substantially complete, the organic layer was decanted from the aqueous layer onto potassium hydroxide and dried. This diazomethane formation and addition was repeated using identical quantities of diethyl ether and sodium hydroxide and 30 g of N(methyl)-N(nitro)-N(nitroso)-guanidine. The resultant diazomethane reactant was then added to the mixed anhydride solution prepared above and the reaction mixture was allowed to react to cold (–30° C.) for approximately 20 minutes. When the reaction was substantially complete, as indicated by TLC, nitrogen was bubbled through the solution using a fire polished Pasteur pipet to remove any excess diazomethane and then the solution was concentrated under reduced pressure to provide a residue. This residue was purified using flash chromatography (eluent of 10% ethyl acetate in methylene chloride) to provide 13.62 g of a yellow oil.

Yield: 83%.

H NMR (CDCl$_3$): δ 3.32–3.46 (m, 2H), 4.40–4.67 (m, 1H), 5.00–5.09 (m, 2H), 5.44 (s, 1H), 5.76 (d, J=7.8 Hz, 1H), 7.25–7.86 (m, 12H).

C. (3R) Benzyl 2-aza-3-(naphth-2-ylthiomethyl)-4-oxo-5-chloro pentanoate

A short burst (about 2 seconds) of anhydrous hydrochloric acid (gas) was passed through a cold (–20° C.) solution of 13.62 g (33.59 mmol) of the subtitled intermediate from Preparation 3B in 230 mL of diethyl ether, resulting in the evolution of a gas. This procedure was repeated taking care not to add excess hydrochloric acid. When the reaction was substantially complete, as indicated by TLC, the solution was concentrated under reduced pressure to provide a residue. This residue was purified using flash chromatography (eluent of 10% ethyl acetate in methylene chloride) to provide 12.05 g of a pale tan solid.

Yield: 87%.

H NMR (CDCl$_3$): δ 3.41 (dd, J=12,6 Hz, 1H), 3.53 (dd, J=12,6 Hz, 1H), 4.18 (AB q, J=41.9 Hz, J=15.9 Hz, 2H), 4.77 (dd, J=9, 3 Hz, 1H), 5.04 (AB q, J=12 Hz, J=10.4 Hz, 2H), 5.59 (d, J=7 Hz, 1H), 7.24–7.85 (complex, 12H).

[α]$_D$ –80.00° (c 1.0, MeOH).

IR (CDCl$_3$): 3426, 3031, 3012, 1717, 1502, 1340, 1230, 1228, 1045 cm$^{-1}$.

MS (FD): m/e 413 (M⁺), 413 (100).

Analysis for $C_{22}H_{20}NO_3SCl$: Calcd: C, 63.84; H, 4.87; N, 3.38; Found: C, 64.12; H, 4.95; N. 3.54.

D. [3R-(3R*,4S*)]Benzyl 2-aza-3-(naphth-2-ylthiomethyl)-4-hydroxy-5-chloro pentanoate To a cold (0° C.) solution of 530 mg (1.28 mmol) of the subtitled intermediate of Preparation 3C, in 10 mL of tetrahydrofuran and 1 mL of water, was added 73 mg (1.92 mmol) of sodium borohydride. When the reaction was substantially complete as indicated by TLC, the solution was adjusted to pH 3 using 10 mL of an aqueous saturated ammonium chloride solution and 500 μL of a 5N hydrochloric acid solution. The resultant solution was extracted twice with methylene chloride and the combined organic layers were washed with water, dried over sodium sulfate, filtered and then concentrated under reduced pressure to provide a residue. This residue was purified using radial chromatography (eluent of methylene chloride) to provide 212 mg of a tan solid.

Yield: 40%.

H NMR (CDCl₃): δ 3.40 (s, 2H), 3.61–3.71 (m, 2H), 3.97–3.99 (m, 2H), 4.99 (s, 2H), 5.16 (br.s, 1H), 7.21–7.83 (complex, 12H).

MS (FD): m/e 415 (M⁺), 415 (100).

$[\alpha]_D$ −47.67° (c 0.86, MeOH).

IR (CHCl₃): 3630, 3412, 3011, 1720, 1502, 1236, 1044 cm⁻¹.

Analysis for $C_{22}H_{22}NO_3ClS$: Calcd: C, 63.53; H, 5.33; N, 3.37; Found: C, 63.72; H, 5.60; N. 3.64.

E. [3R-(3R*,4S*)]Benzyl 2-aza-3-oxiranyl-4-naphth-2-ylthio butanoate

A solution of 31 mg (0.55 mmol) of potassium hydroxide in 1 mL of ethanol was added to a solution of 190 mg 0.46 mmol of the subtitled intermediate of Preparation 3D, in 6 mL of a 1:2 ethanol/ethyl acetate solution. When the reaction was substantially complete, as indicated by TLC, the reaction mixture was poured into a water/methylene chloride mixture. The resulting layers were separated, and the organic layer was washed with water, dried over sodium sulfate, filtered and then concentrated under reduced pressure to provide a residue. This residue was purified using radial chromatography (eluent of 10% ethyl acetate in methylene chloride) to provide 172 mg of a light tan solid.

Yield: 99%.

H NMR (CDCl₃): δ 2.76 (br.,s 2H), 3.01 (br.s, 1H), 3.31 (d=5 Hz, 2H), 3.77 (br.s, 1H), 5.05 (s, 2H), 5.22 (d, J=6 Hz, 1H), 7.25–7.85 (complex, 12H).

$[\alpha]_D$ −125.42° (c 0.59, MeOH).

MS (FD): m/e 379 (M⁺), 379 (100).

IR (CHCl₃): 3640, 3022, 2976, 1720, 1502, 1235, 1045 cm⁻¹.

Analysis for $C_{22}H_{21}NO_3S$: Calcd: C, 69.63; H, 5.58; N, 3.69; Found: C, 69.41; H, 5.53; N. 3.64.

F. [3R-(3R*,4R*,4a'S*,8a'S*)]Benzyl, [2-aza-3-(naphth-2-ylthiomethyl)-4-hydroxy-5-(3'-(1''N (t-butyl)amino-1''-oxomethyl)octahydroisoquinolin-2'-yl)]pentanoate A solution was prepared containing 165 mg (0.40 mmol) of the subtitled intermediate of Preparation 3E and 94 mg (0.43 mmol) of 3-(1-N(t-butyl)amino-1-oxomethyl) octahydro-(2H)-isoquinoline in 5 mL of ethanol. The resulting reaction mixture was allowed to react at 80° C. for approximately 19 hours. The solution was then cooled to room temperature and concentrated under reduced pressure to provide a residue. This residue was purified using radial chromatography (eluent of 10% ethyl acetate in methylene chloride) to provide 103 mg of an off-white foam.

Yield: 42%.

H NMR (CDCl₃): δ 1.10–1.73 (m, 20H), 2.13–2.31 (m, 2H), 2.44–2.53 (m, 1H), 2.56–2.68 (m, 1H), 2.86–2.97 (m, 1H), 3.52 (br.s, 2H), 4.02 (br.s, 2H), 4.98 (s, 2H), 5.65 (s, 1H), 5.94 (s, 1H), 7.25–7.83 (complex, 13H).

MS (FD): m/e 629 (M⁺), 138 (100).

$[\alpha]_D$ −92.45° (c 1.06, MeOH).

IR (CHCl₃): 3429, 3010, 2929, 1713, 1670, 1514, 1455, 1047 cm⁻¹.

Analysis for $C_{35}H_{47}NO_4S$: Calcd: C, 69.98; H, 7.67; N, 6.80; Found: C, 69.86; H, 7.78; N. 6.58.

G. [2R-(2R*,3R*,4a'S*,8a'S*)]-N (t-butyl)-2'-[2-hydroxy-3-amino-4-(naphth-2-ylthio)] butyl octohydroisoquinoline-3'-carboxamide A solution was prepared containing 50 mg (0.081 mmol) of the subtitled intermediate of Preparation 3F and 1 mL of a 38% aqueous hydrobromic acid solution in acetic acid. The resultant reaction mixture was allowed to react at room temperature for approximately 1 hour and then was concentrated under reduced pressure to provide a residue. This residue was slurried with toluene and then concentrated under reduced pressure to provide 61 mg of the desired subtitled intermediate. This compound was used crude without purification in Example 9.

H NMR (CDCl₃): δ 1.14 (s, 1H), 1.17–2.07 (complex, 15H), 2.66–2.87 (m, 2H), 3.21–3.25 (m, 2H), 3.75 (d, J=12 Hz, 1H), 3.85 (d, J=6 Hz, 1H), 4.36–4.47 (m, 1H), 6.73 (s, 1H), 7.39–7.90 (complex, 7H).

MS (FD): m/e 483 (M⁺), 483 (100).

Preparation 4

A. (2R)-2-N(benzyloxycarbonyl)amino-3-phenylthio propanoic acid

The desired subtitled intermediate was prepared substantially in accordance with the procedure detailed in Procedure 3A, using 13.1 mL (127 mmol) of thiophenol, 4.6 g (117 mmol) of a 60% sodium hydride solution and 25.6 g (116 mmol) of (L)-N(benzyloxycarbonyl)serine β-lactone in 450 mL of tetrahydrofuran to provide a residue. This residue was purified using flash chromatography (gradient solution of 0–2% acetic acid in a 4:1 methylene chloride/ethyl acetate mixture) to provide 27.9 g of a white solid.

Yield: 72%.

H NMR (CDCl₃): δ 7.55–7.18 (m, 10H), 5.55 (d, J=7 Hz, 1H), 5.08 (s, 2H), 4.73–4.60 (m, 1H), 3.55–3.30 (m, 2H).

IR (KBr): 3304, 3035, 1687, 1532, 736 cm⁻¹.

MS (FD): m/e 332, 288, 271, 181.

Analysis for $C_{17}H_{17}NO_4S$: Calcd: C, 61.61, H, 5.17; N, 4.23; Found: C, 61.69; H, 5.22; N, 4.47.

B. (3R) Benzyl 2-aza-3-(phenylthiomethyl)-4-oxo-5-diazo pentanoate

The desired subtitled compound was prepared substantially in accordance with the procedure detailed in Procedure 3B, using 12.1 g (37 mmol) of the subtitled compound of Preparation 4A, 5.09 mL (37 mmol) of triethylamine, 7.13 mL (55 mmol) isobutyl chloroformate, 146 mmol of a diazomethane solution to provide a residue. The diazomethane solution was prepared using 100 mL of diethyl ether, 150 mL of a 5N sodium hydroxide solution and 21 (146 mmol) of N(methyl)-N(nitro-N(nitroso)-guanidine as described in Preparation 3B. This residue was purified using flash chromatography (gradient eluent of 0–5% ethyl acetate in methylene chloride) to provide a yellow oil.

Yield: 73%.

H NMR (CDCl₃): δ 7.50–7.19 (m, 10H), 5.62 (d, J=7 Hz, 1H), 5.47 (br.s, 1H), 5.11 (s, 2H), 4.50–4.32 (m, 1H), 3.33 (d, J=6 Hz, 1H).

IR (KBr): 3012, 2115, 1720, 1501, 1367, 1228 cm$^{-1}$.
MS (FD): m/e 356, 328, 242.

C. (3R) Benzyl, 2-aza-3-(phenylthiomethyl)-4-oxo-5-chloro pentanoate

The desired subtitled compound was prepared substantially in accordance with the procedure detailed in Procedure 3C, using 22.3 g (63 mmol) of the subtitled compound of Preparation 4B and small quantities of hydrochloric acid (gas) in 400 mL of diethyl ether to provide 21 g of a white solid. This solid was used without further purification.

H NMR (CDCl$_3$): δ 7.50–7.15 (m, 10H), 5.56 (dd, J=2, 6.7 Hz, 1H), 5.11 (s, 2H), 4.78–4.67 (m, 1H), 4.20 (d, J=15.9 Hz, 1H), 4.12 (d, J=15.9 Hz, 1H), 3.48–3.23 (m, 2H).
IR (KBr): 3349, 1732, 1684, 1515, 1266 cm$^{-1}$.
MS (FD): m/e 363 (M$^+$).
Analysis for C$_{18}$H$_{18}$NO$_3$SCl: Calcd: C, 59.42, H, 4.99; N, 3.85; Found: C, 59.57; H, 5.09; N, 4.13.

D. [3R-(3R*,4S*)]Benzyl 2-aza-3-(phenylthiomethyl)-4-hydroxy-5-chloro pentanoate The desired subtitled compound was prepared substantially in accordance with the procedure detailed in Procedure 3D, using 21 g (58 mmol) of the subtitled compound of Preparation 4C, 2.4 g (63 mmol) of sodium borohydride in 300 mL of tetrahydrofuran to provide a residue. This residue was purified using flash chromatography (gradient eluent of 0–2% methanol in methylene chloride) followed by flash chromatography (gradient eluent of 0–2% ethyl acetate in chloroform) and then recrystallized from methylene chloride at −78° C. to provide 8.3 g of the subtitled compound.
Yield: 39%.
$^1$NMR (CDCl$_3$): δ 7.47–7.19 (m, 10H), 5.22–5.03 (m, 1H), 5.09 (s, 2H), 4.01–3.89 (m, 2H), 3.75–3.58 (m, 2H), 3.32 (d, J=4 Hz, 2H).
IR (KBr): 3321, 2951, 1688, 1542, 1246, 738 cm$^-$.
MS (FD): m/e 366 (M$^+$), 119.
Analysis for C$_{18}$H$_{20}$NO$_3$SCl: Calcd: C, 59.09; H, 5.51; N, 3.83; Found: C, 59.03, H, 5.50; N, 3.96.

E. [3R-(3R*,4S*)]Benzyl 2-aza-3-oxiranyl-4-phenylthio butanoate

The desired subtitled compound was prepared substantially in accordance with the procedure detailed in Procedure 3E, using 8.3 g (23 mmol) of the subtitled compound of Preparation 4D, 1.4 g (25 mmol) of potassium hydroxide in 400 mL of ethanol to provide a residue. This residue was purified using flash chromatography (gradient eluent of 0–2% ethyl acetate in methylene chloride) to provide 6.4 g of a white solid.
Yield: 85%.
$^1$NMR (CDCl$_3$): δ 7.45–7.15 (m, 10H), 5.12 (s, 1H), 5.08 (s, 2H), 3.77–3.62 (m, 1H), 3.21 (d, J=6 Hz, 2H), 2.99 (m, 1H), 2.77 (m, 2H).
IR (KBr): 3303, 3067, 1694, 1538, 1257, 741 cm$^-$.
MS (FD): m/e 329.
Analysis for C$_{32}$H$_{45}$NO$_3$O$_4$S: Calcd: C, 65.63; H, 5.81; N, 4.25; Found: C, 65.48, H, 5.82; N, 4.29.

F. [3R-(3R*,4R*,3'S*,4a'S*,8a'S*]Benzyl, [2-aza-3-(phenylthiomethyl)-4-hydroxy-5-(3'-(1"-N (t-butyl)amino-1"-oxomethyl)octohydroisoquinolin-2'-yl)]pentanoate The desired subtitled compound was prepared substantially in accordance with the procedure detailed in Procedure 3F, using 6.3 g (19 mmol) of the subtitled compound of Preparation 4E, 5 g (21 mmol) of 3-[N(t-butyl)aminocarbonyl]octohydro-(2H)-isoquinoline in 300 mL of ethanol to provide a residue. This residue was purified using flash chromatography (gradient eluent of 0–20% ethyl acetate in methylene chloride) to provide 4.3 g of a white solid.
Yield: 40%.

$^1$NMR (CDCl$_3$): δ 7.41–7.11 (m, 10H), 5.90 (d, J=5 Hz, 1H), 5.64 (s, 1H), 5.05 (d, J=4 Hz, 2H), 4.08–3.90 (m, 2H), 3.40 (d, J=6, 2H), 3.05 (s, 1H), 2.95–2.85 (m, 1H), 2.62–2.45 (m, 2H), 2.28–2.15 (m, 2H), 2.05–1.88 (m, 2H), 1.78–1.10 (m, 7H), 1.29 (s, 9H).
IR (KBr): 3330, 2925, 2862, 1706, 1661, 1520, 1424, 1246, 738, 694 cm$^-$.
MS (FD): m/e 568 (M$^+$), 467.
Analysis for C$_{32}$H$_{45}$N$_3$O$_4$S: Calcd: C, 67.69; H, 7.99; N, 7.40; Found: C, 67.64, H, 8.20; N, 7.45.

G. [2R-(2R*,3R*,3'S*,4a'S*,8a'S*]N (t-butyl)-2'-[2-hydroxy-3-amino-4-(naphth-2-ylthio)]butyl octohydroisoquinoline-3'-carboxamide The desired subtitled compound was prepared substantially in accordance with the procedure detailed in Procedure 3G using 1 g (1.8 mmol) of the subtitled compound of Preparation 4F and 40 mL of a 30% hydrobromic acid in acetic acid solution, with the exception that the crude material was dissolved in 30 mL of methanol. To the resulting solution, was added 2 mL of diethylamine and 2 mL of concentrated ammonium hydroxide and then the mixture was concentrated under reduced pressure to provide a residue. This residue was redissolved in water and ethyl acetate. The resulting layers were separated and the organic layer was washed sequentially with an aqueous sodium bicarbonate solution and brine, dried over sodium sulfate, filtered and then reduced to dryness under reduced pressure to provide a residue. This residue was purified using flash chromatography (gradient eluent of 0–10% methanol in chloroform (containing 3 drops of ammonium hydroxide per 1000 mL of chloroform) to provide 0.54 g of a white foam.
Yield: 71%.
$^1$NMR (CDCl$_3$): δ 7.41–7.16 (m, 5H), 6.07 (s, 1H), 3.78–3.70 (m, 1H), 3.45–3.38 (m, 1H), 3.03–2.84 (m, 3H), 2.38–2.20 (m, 3H), 2.00–1.05 (m, 12H), 1.33 (s, 9H).
IR (KBr): 2924, 2862, 1660, 1517, 1454, 1439, 737, 691 cm$^-$.
MS (FD): m/e 434 (M$^+$), 293.

EXAMPLE 1

[1S-(1R*,4S*,5S*)]-N-[1-(2'-amino-2'-oxoethyl)-2-oxo-3 -aza-4-naphth-2-ylthiomethyl-5-hydroxy-6-(2"-(1'"-N(t-butyl) amino-1'"-oxomethyl)phenyl)]hexyl quinolin-2-ylcarboxamide To a solution of 100 mg (0.237 mmol) of the subtitled intermediate of Preparation 1E in a 2.5 mL of a 4:1 solution of tetrahydrofuran/dimethylformamide, was added 71.5 mg (0.249 mmol) of (S)-2-(2-N-quinolinyl-carboxy) -2,4-diamino-1,4-butanedioic acid, and 32.5 mg (0.241 mmol) of HOBT·H$_2$O. This mixture was cooled to −10° C. before adding 49.6 mg (0.241 mmol) of dicyclohexylcarbodiimide (DCC). After approximately one hour, the reaction mixture was warmed to room temperature and allowed to react overnight. The reaction was then cooled to 0° C. and filtered to remove a white precipitate. The filtrate was concentrated under reduced pressure to provide a residue which was redissolved in 25 mL of ethyl acetate and washed sequentially with a saturated sodium bicarbonate solution, water, a 5% citric acid solution and brine. The resulting layers were separated and the organic layer was dried over sodium sulfate, filtered and then concentrated under reduced pressure to provide a colorless foam. This foam was purified using flash chromatography (eluent of 5% methanol in methylene chloride) followed by high performance liquid chromatography (eluent of 20–25% water in methanol) to provide 93 mg of a white solid.

Yield: 71%.

$^1$NMR (CDCl$_3$): δ 9.29 (d, J=7 Hz, 1H), 8.10 (m, 3H), 7.54–7.77 (m, 8H), 7.15–7.33 (m, 7H), 6.60 (br.s, 1H), 6.30 (s, 1H), 5.92 (br.s, 1H), 4.95 (m, 1H), 4.27 (m, 1H), 3.93 (m, 1H), 3.47 (m, 1H), 3.30 (m, 1H), 2.76–3.02 (m, 4H), 1.42 (s, 9H).

MS (FD): m/e 692 (M$^+$), 691 (100).

Analytical for C$_{39}$H$_{41}$N$_5$O$_5$S: Calcd: C, 67.71; H, 5.97; N, 10.12; Found: C, 67.97, H, 5.94; N, 9.96.

EXAMPLE 2

A. [2'R-(2'R*,3'R*,6'S*)]-N(t-butyl)-2-[ 2'-hydroxy-3'-naphth-2-ylthiomethyl-4'-aza-5',8'-dioxo -6'-(N(t-butoxycarbonyl)amino-8'-amino]octyl benzamide The subtitled compound was prepared substantially in accordance with the procedure detailed in Example 1 using 0.50 g (1.18 mmol) of the subtitled intermediate of Preparation 1E, 0.289 (1.24 mmol) of (2S)-2-N(t-butoxycarbonyl-3-carbamoyl propanoic acid 0.163 g (1.21 mmol) of HOBT·H$_2$O and 0.249 g (1.21 mmol) of DCC in 11.5 mL of a 10:1.5 solution of tetrahydrofuran/dimethylformamide to provide a white solid. This solid was purified using flash chromatography (gradient eluent of 1–5% methanol in methylene chloride) to provide 0.64 g of the desired subtitled compound.

Yield: 85%.

$^1$NMR (CDCl$_3$): δ 7.71–7.81 (m, 4H), 7.17–7.48 (m, 7H), 6.38 (br.s, 1H), 6.25 (br.s, 1H), 5.98 (m, 1H), 5.81 (br.s, 1H), 4.41 (m, 1H), 4.19 (m, 1H), 3.87 (m, 1H), 3.44 (m, 1H), 3.27 (m, 1H), 2.52–2.91 (m, 4H), 1.43 (s, 9H).

MS (FD): m/e 637 (M$^+$), 636 (100).

Analysis for C$_{34}$H$_{44}$N$_4$O$_6$S: Calcd: C, 64.13; H, 6.96; N, 8.80; Found: C, 64.09, H, 6.90; N, 8.81.

B. [2'R-(2'R*,3'R*,6'S*)]-N(t-butyl)-2-[2'-hydroxy-3'-naphth-2-ylthiomethyl-4'-aza-5',8'-dioxo-6',8'-diamino] octyl benzamide The subtitled compound was prepared substantially in accordance with the procedure detailed in Preparation 1E using 0.64 g (1.00 mmol) of the subtitled intermediate of Example 2A in 10 mL of 15% trifluoroacetic acid in methylene chloride to provide a white foam. This foam was purified using flash chromatography (gradient eluent of 5–10% methanol in methylene chloride) to provide a white solid.

$^1$NMR (CDCl$_3$): δ 7.71–7.93 (m, 4H), 7.17–7.47 (m, 7H), 6.18–6.39 (m, 2H), 5.71 (m, 1H), 4.23 (m, 1H), 3.89 (m, 1H), 3.59 (m, 1H), 3.33–3.45 (m, 3H), 2.76–2.97 (m, 2H), 2.60 (m, 1H), 1.80–2.26 (m, 4H), 1.45 (s, 9H).

MS (FD): m/e 537 (M$^+$), 536 (100).

C. [2'R-(2'R*,3'R*,6'S*)]-N(t-butyl)-2-[2'-hydroxy -3'-naphth-3-ylthiomethyl-4'-aza-5',8'-dioxo-6'-(N-benzyloxycarbonyl) amino-8'-amino]octyl benzamide A solution of 0.032 g (0.19 mmol) of benzylchloroformate in 1 mL of methylene chloride was added dropwise to a cold (0° C.) solution containing 0.10 g (0.19 mmol) of the subtitled intermediate of Example 2B and 0.026 mL (0.19 mmol) of triethylamine in 5 mL of methylene chloride. The resulting reaction mixture was allowed to react for approximately one hour at 0° C. and then overnight at room temperature. The reaction was diluted with water and the resulting layers were separated and the organic layer was washed sequentially with a saturated sodium bicarbonate solution, water, a 5% citric acid solution and brine, dried over sodium sulfate, filtered and then concentrated under reduced pressure to provide a white foam. This foam was purified using flash chromatography (eluent of ethyl acetate) to provide 34 mg of the desired subtitled compound.

Yield: 29%.

$^1$NMR (CDCl$_3$): δ 7.71–7.82 (m, 4H), 7.17–7.48 (m, 12H), 6.22 (m, 3H), 5.74 (m, 1H), 5.08 (s, 2H), 4.47 (m, 1H), 4.21 (m, 1H), 3.87 (m, 1H), 3.23–3.47 (m, 4H), 2.80 (m, 3H), 2.62 (m, 1H), 1.46 (s, 9H).

MS (FD): m/e 671 (M$^+$), 670 (100).

Analysis for C$_{37}$H$_{42}$N$_4$O$_6$S: Calcd: C, 66.25; H, 6.31; N, 8.35; Found: C, 66.06, H, 6.37; N, 8.08.

EXAMPLE 3

[1S-(1R*,4S*,5S*)]-N-[1-(2'-amino-2'-oxoethyl)
-2-oxo-3-aza-4-phenylthiomethyl-
5-hydroxy-6-(2"-(1"'-N(t-butyl)
amino-1"'-oxomethyl]phenyl))hexyl
quinolin-2-ylcarboxamide The desired titled compound was prepared substantially in accordance with the procedure detailed in Example 1 using the subtitled intermediate of Preparation 2E and (S)-2-N(quinolin-2-ylcarbonyl)amino-3-carbamoyl propanoic acid to provide 116 mg of the desired titled compound.

Yield: 58%.

$^1$NMR (CDCl$_3$): δ 9.33 (d, J=8 Hz, 1H), 8.29 (q, J=9 Hz, 2H), 8.18 (d, J=9 Hz, 1H), 7.88 (d, J=8 Hz, 1H), 7.79 (m, 1H), 7.64 (m, 1H), 7.08–7.42 (m, 9H), 6.03 (m, 2H), 5.89 (d, J=6 Hz, 1H), 5.47 (m, 1H), 4.93 (m, 1H), 4.23 (m, 1H), 3.90 (m, 1H), 3.32 (m, 2H), 2.79–3.03 (m, 4H), 1.47 (s, 9H).

MS (FD): m/e 642 (M$^+$), 642 (100).

Analysis for C$_{35}$H$_{39}$N$_5$O$_5$S: Calcd: C, 65.50; H, 6.12; N, 10.91; Found: C, 65.25, H, 6.13; N, 10.80.

EXAMPLE 4

A. [2'R-(2'R*,3'R*,6'S*)]-N(t-butyl) -2-[2'-hydroxy-3'-phenylthiomethyl-4'-aza-5',8'-dioxo-6'-(N (t-butoxycarbonyl)amino-8'-amino]octyl benzamide The desired subtitled compound was prepared substantially in accordance with the procedure detailed in Example 2A using 0.545 g (1.47 mmol) of the subtitled intermediate of Preparation 1E, 0.202 g (1.50 mmol) of HOBT·H$_2$O, 0.309 g (1.50 mmol) of DCC and 0.358 g (1.54 mmol of 2-N(t-butoxycarbonyl)-3-carbamoyl propanoic acid.

Yield: 64%.

$^1$NMR (CDCl$_3$): δ 7.16–7.43 (m, 9H), 5.84–5.99 (m, 4H), 5.41 (m, 1H), 4.39 (m, 1H), 4.18 (m, 1H), 3.84 (m, 1H), 3.23–3.38 (m, 2H), 2.78–2.97 (m, 3H), 2.59 (m, 1H), 1.47 (s, 9H).

MS (FD): m/e 587 (M$^+$), 587 (100).

Analysis for C$_{30}$H$_{42}$N$_4$O$_6$S: Calcd: C, 61.41; H, 7.22; N, 9.55; Found: C, 61.49, H, 7.18; N, 9.26.

B. [2'R-(2'R*,3'R*,6'S*)]-N(t-butyl)-2-[ 2'-hydroxy-3'-phenylthiomethyl-4'-aza-5=,8'-dioxo-6',8'-diamino]octyl benzamide The subtitled compound was prepared substantially in accordance with the procedure detailed in Example 2B using 0.381 (0.65 mmol) of the subtitled compound of Example 4A and 2.25 mL of trifluoroacetic acid.

Yield: 99%.

MS (FD): m/e 487 (M$^+$), 487 (100).

C. [2'R-(2'R*,3'R*,6'S*)]-N(t-butyl)-2-[ 2'-hydroxy-3'-phenylthiomethyl-4'-aza-5',8'-dioxo-6' -(N-(benzyloxycarbonyl)amino-8'-amino]octyl benzamide The subtitled compound was prepared substantially in accordance with the procedure detailed in Example 2C using the subtitled compound isolated from Example 4B.

Yield: 82 mg (50%).

$^1$NMR (CDCl$_3$): δ 7.12–7.40 (m, 14H), 6.18 (d, J=7 Hz, 1H), 5.99 (s, 1H), 5.91 (d, J=6 Hz, 2H), 5.45 (br.s, 1H), 5.12 (m, 2H), 4.44 (m, 1H), 4.15 (m, 1H), 3.84 (m, 1H), 3.20–3.35 (m, 2H), 2.78–2.96 (m, 3H), 2.59 (m, 1H), 1.47 (s, 9H).

MS (FD): m/e 621 (M$^+$), 621 (100).

Analysis for C$_{33}$H$_{40}$N$_4$O$_6$S: Calcd: C, 63.85; H, 6.50; N, 9.03; Found: C, 63.67, H, 6.34; N, 8.91.

EXAMPLE 5

[2R-(2R*,3R*,3'S*,4a'S*,8a'S*)]-N
(t-butyl)-2'-[2-hydroxy-3-naphth-
2-ylthiomethyl-4,7-diaza-5,8-dioxo
-6-(2''-amino-2''-oxoethyl)-8-quinolin-2-yl]octyl
decahydroisoquinoline-3'-carboxamide To a cold (−10° C.) solution containing 0.48 mmol of the subtitled intermediate of Preparation 3G, 146 mg (0.51 mmol) of (S)-2-(N(quinolin-2-ylcarbonyl)amino-3-carbamoyl propanoic acid, 69 mg (0.51 mmol) of 1-hydroxybenztriazole hydrate (HOBT·H$_2$O) and 160 mL (1.45 mmol) of N-methylmorpholine (NMM) in 10 mL of anhydrous tetrahydrofuran, was added 102 mg (0.49 mmol) of 1,3-dicyclohexylcarbodiimide (DCC). The resulting reaction mixture was allowed to react at room temperature for approximately 72 hours and then was recooled in an ice-acetone bath and filtered. The filtrate was reduced to dryness under reduced pressure to provide a residue. This residue was redissolved in ethyl acetate, washed sequentially with water, 10% citric acid, a saturated sodium bicarbonate solution and a brine solution, dried over sodium sulfate, filtered and then concentrated under reduced pressure to provide a residue. This residue was purified using radial chromatography (eluent of 5% methanol in methylene chloride) to provide 11 mg of a colorless foam.

Yield: 31%.

$^1$NMR (CDCl$_3$): δ 1.08–2.48 (complex, 27H), 2.64–2.81 (m, 1H), 2.82–2.95 (m, 1H), 2.99–3.07 (m, 1H), 3.31–3.45 (m, 2H), 4.07–4.14 (m, 1H), 4.20–4.26 (m, 1H), 4.94–4.98 (br.s, 1H), 6.03 (br.s, 1H), 6.37 (br.s, 1H), 7.29–7.36 (m, 3H), 7.56–7.81 (m, 8H), 8.09–8.91 (m, 3H), 9.19 (d, J=7 Hz, 1H),

[α]$_D$ −79.49° (c 0.78, MeOH).

IR (CHCl$_3$) 3328, 3055, 2924, 2861, 1661, 1521, 1500 cm$^{-1}$.

MS (FD): m/e 652 (M$^+$), 652 (100).

Analysis for C$_{42}$H$_{52}$N$_6$O$_5$S: Calcd: C, 66.99; H, 6.96; N, 11.16; Found: C, 66.80, H, 6.98; N, 10.91.

EXAMPLE 6

[2R-(2R*,3R*,3'S*,4a'S*,8a'S*)]-N
(t-butyl)-2'-[2-hydroxy-3-
phenylthiomethyl-4,7-diaza-5,8-dioxo
-6-(2''-amino-2''-oxoethyl)-8-quinolin-2-yl] octyl
decahydroisoquinoline-3'-carboxamide The desired titled compound was prepared substantially in accordance with the procedure detailed in Example 1 using 0.5 g (1.16 mmol) of the subtitled intermediate of Preparation 4G, 0.37 g (1.37 mmol) of (S)-2-N(quinolin-2-ylcarbonyl)amino-3-carbamoyl propanoic acid, 0.17 g (1.27 mmol) of HOBT·H$_2$O, 0.25 mL (1.24 mmol) of N-methylmorpholine and 0.26 g (002.4 mol) of DCC was dissolved in 20 mL of tetrahydrofuran to provide a residue. This residue was purified using flash chromatography (gradient solution of 0–5% methanol in chloroform) followed by high performance liquid chromatography to provide 0.51 g of a white solid.

Yield: 63%.

$^1$NMR (CDCl$_3$): δ 9.22 (d, J=7.5 Hz, 1), 8.30–7.05 (m, 12H), 6.13 (br.s, 1H), 5.85 (s, 1H), 5.65 (br.s, 1H) 5.00–4.96 (m, 1H), 4.30–3.80 (m, 3H), 2.39–3.28 (m, 2H), 3.02–2.85 (m, 3H), 2.65–2.60 (m, 1H), 2.57 (d, J=7 Hz, 1H), 2.35–2.20 (m, 2H), 2.00–1.15 (m, 17H), 1.38 (s, 9H).

IR (KBr): 3009, 2929, 2867, 1673, 1549, 1500, 1222 cm$^{-1}$.

MS (FAB): m/e 703 (M$^+$), 602.

Analytical for C$_{38}$H$_{50}$N$_6$O$_5$S: Calcd: C, 64.93; H, 7.17; N, 11.96; Found: C, 64.81, H, 7.29; N, 11.71.

As noted above, the compounds of the present invention are useful for inhibiting HIV protease which is associated with viral component production and assembly. An embodiment of the present invention is a method of treating or preventing HIV infection comprising administering to a primate in need thereof an effective amount of a compound of formula I or a pharmaceutically acceptable salt thereof. Another embodiment of the present invention is a method of treating or preventing AIDS comprising administering to a primate in need thereof an effective amount of a compound of formula I or a pharmaceutically acceptable salt thereof. A further embodiment of the present invention is a method of inhibiting HIV replication comprising administering to an HIV infected cell, a cell susceptible to HIV infection or a primate in need thereof, an effective amount of a compound of formula I or a pharmaceutically acceptable salt thereof.

The term "effective amount" as used herein, means an amount of a compound of the present invention which is capable of inhibiting the HIV protease mediated viral component production and assembly. The HIV protease inhibition contemplated by the present method includes either therapeutic or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Methanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules, which, after mixing, are compressed on a tablet machine to yield tables each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredients, cellulose, starch and magnesium stearate and blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The following experiment (Fluorescence HIV-1 Protease Inhibitor Assay) was carried out to demonstrate the ability of the compounds of the present invention to inhibit HIV protease.

As used herein, the abbreviations are defined as follows:
BSA—bovine serum albumin
BOC—t-butyloxycarbonyl
BrZ—2-bromobenzyloxycarbonyl
2-ClZ—2-chlorobenzyloxycarbonyl
DCC—dicyclohexylcarbodiimide
DIEA—diisopropylethylamine
DTT—dithiothreitol
EDTA—ethylenediaminetetraacetic acid
FITC—fluorescein isothiocarbamyl
HEPES—4-(2-hydroxyethyl)-1-piperazine-ethanesulfonic acid
MES—4-morpholineethanesulfonic acid
PAM—phenylacetimidomethyl
TAPS—3-[tris(hydroxymethyl)methyl]amino-1-sulfonic acid
TRIS—tris(hydroxymethyl) aminomethane
TOS—p-toluenesulfonyl (tosyl)

I. Preparation of Protease and gag fractions

A. Culture of *E. coli* K12 L507/pHP10D

Lyophils of *E. coli* K12 L507/pHP10D were obtained from the Northern Regional Research Laboratory, Peoria, Ill., 61604, under the accession number NRRL B-18560 (deposited Nov. 14, 1989). The lyophils were decanted into tubes containing 10 mL LB medium (10 g Bacto-tryptone, 5 g Bacto-yeast extract, and 10 g aqueous sodium chloride per liter; the pH was adjusted to 7.5 and incubated at 32° C., overnight).

A small portion of the overnight culture was placed on LB-agar (LB medium with 15 g/L Bacto-agar) plates containing 12.5 µg/mL tetracycline in a manner so as to obtain a single colony isolate of *E. coli* K12 L507/pHP10D. The single colony obtained was inoculated into 10 mL of LB medium containing 12.5 µg/mL tetracycline and incubated overnight at 32° C. with vigorous shaking. The 10 mL overnight culture was inoculated into LB medium containing 12.5 µg/mL tetracycline and incubated at 32° C. with vigorous shaking until the culture reached mid-log phase.

B. Culture of *E. coli* K12 L507/pHGAG

Lyophils of *E. coli* K12 L507/pHGAG were obtained from the NRRL under the accession number NRRL B-18561 (deposited Nov. 14, 1989). A purified colony of *E. coli* K12 L507/pHGAG was isolated, and used an inoculum for a culture which was grown to mid-log phase in substantial accordance with the teaching of Step A, above, for *E. coli* K12 L507/pHP10D.

C. Preparation of Protease Fraction

A culture of *E. coli* K12 L507/pHP10D was grown to mid-log phase at 32° C. in LB media containing 12.5 µg/mL tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 mL 50 mmol MES buffer (pH 6.0) containing 1 mmol EDTA, 1 mmol DDT, 1 mmol PMSF and 10% glycerol ("Buffer A"). Cells were lysed by sonication using a Fischer Model 300 Dismembrator and a microtip probe. Following centrifugation at 27,000×g, the supernatant was diluted to a total volume of 60 mL with Buffer A and loaded onto a 2.0×19 cm QAE-Sepharose column (1 mL/min, 4° C.), that had been equilibrated in Buffer A. The column was washed isocratically for 180 min and then eluated with a gradient eluent of 0–1.0M aqueous solution chloride in Buffer A over 120 min. Enzymatic activity was measured by HPLC using the synthetic peptide SQNYPIV as described in Margolin et al., *Biochem. Biophys. Res. Commun.*, 167, 554–560 (1990); the production of the p1 peptide (SQNY) was measured.

The active fractions were combined, made 1.2M in ammonium sulfate, and applied to a 2.0×18 cm hexyl agarose column that had been equilibrated in Buffer A containing 1.2M ammonium sulfate. The sample was loaded at a flow rate of 1 mL/min at 4° C., washed with the equilibration buffer for 240 min (1 mL/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 mL using an Amicon stirred cell with a YM-10 membrane and then applied to a MonoS cation exchange column (1.0×10 cm) that had been equilibrated in Buffer A. The sample was loaded at a flow rate of 1 mL/min at 25° C. After washing isocratically for 30 min, the protease was eluted using a linear gradient of 0–0.45M aqueous sodium chloride in Buffer A over 40 min. The column was washed isocratically in Buffer A containing 0.45M aqueous sodium chloride for 30 min.

The active fractions were combined and concentrated to 200 µL using an Amicon stirred cell and a YM-10 membrane and then the protease was applied to a Superose 6 size exclusion column equilibrated in Buffer A containing 0.1M aqueous sodium chloride. The column was washed isocratically in this buffer at a flow rate of 0.5 mL/min, following which the HIV protease was eluted as a single peak.

QAE-Sepharose, and hexyl agarose were purchased from Sigma Chemical Company. Superose 6 and MonoS were purchased from Pharmacia. Buffers and reagents were obtained from Sigma.

D. Preparation of Gag Fraction

In an analogous manner, a culture of *E. coli* K12 507/pHGAG was grown to mid-log phase at 32° C. then shifted to 40° C. for about 4 to 5 hours. The culture was chilled on ice and centrifuged, then the pellet was resuspended in 8 mL lysis buffer containing 5 mg/mL lysozyme. Lysis buffer was comprised of 50 mM Tris-HCl (pH 7.8), 5 mM EDTA, 1 mM DTT, 100 mM NaCl, 1 µg/mL E64 and 2 µg/mL aprotinin. The culture was incubated about 30 to 60 minutes at 60° C., then briefly sonicated in a Branson® Cell Disrupter at 60% power, for three 20 second bursts with chilling between each burst. The culture was then centrifuged at 15,000×g. The supernatant, which contains the unprocessed gag protein, was partially purified by size exclusion chromatography on a Sephadex G-50 column and stored at −20° C. in 50% glycerol and lysis buffer.

II. Preparation of Substrate:
$N^\alpha$-Biotin-Gly-Ser-Gln-Asn-Tyr-Pro-Ile-Val-Gly-Lys ($N^\epsilon$-FITC)-OH A. Preparation of
$N^\alpha$-Biotin-Gly-Ser-Gln-Asn-Tyr-Pro-Ile-Val-Gly-Lys-OH The protected peptide-resin $N^\alpha$-Boc-Gly-Ser-Gln-Asn-Tyr(BrZ)-Pro-Ile-Val-Gly-Lys (2-ClZ)-OCH$_2$-PAM-resin was synthesized on an Advanced Chemtech Model 200 peptide synthesizer at 1.5 mmol scale using the standard double-couple protocol. The amino terminal Boc group was removed with 50% trifluoroacetic acid in methylene chloride and the resulting resin neutralized with 5% di(isopropyl)ethylamine (DIEA) in methylene chloride. Then, 1.1 g (4.5 mmol) of biotin in 20 mL of dimethylsulfoxide was added to the peptide resin, followed by 4.5 mmol of dicyclohexylcarbodiimde (DCC) in 9 mL of methylene chloride. The resulting reaction mixture was diluted to 40 mL total volume using 11 mL methylene chloride, and then allowed to react for approximately 5 hours. The reaction solution was concentrated, the resin washed sequentially with dimethyl sulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (98%).

B. Deprotection

The peptide was deprotected and cleaved from the resin using 50 mL of a hydrofluoric acid/m-cresol solution, 0° C., 1 hour. After removal of the hydrofluoric acid by vacuum distillation, the m-cresol was extracted from the reaction mixture using 100 mL diethyl ether. The peptide was then solubilized in 50% aqueous acetic acid, frozen and lyophilized to provide 2.14 g.

C. Purification

The crude $N^\alpha$-Biotin-Gly-Ser-Gln-Asn-Tyr-Pro-Ile-Val-Gly-Lys-OH was dissolved in 200 mL of a 5% acetonitrile (aqueous) solution containing 0.1% trifluoroacetic acid and then filtered through a 0.22 micron filter. The resulting solution was applied to a 2.2×25 cm. reverse phase column of octadecyl-silica (Vydac C-18) which had been equilibrated with the same buffer. The peptide was eluted using an 855 minute linear gradient of 7.5 to 25% acetonitrile, at 2 mL/minute, with collections of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62%).

Amino acid analysis of the isolated $N^\alpha$-Biotin-Gly-Ser-Gln-Asn-Tyr-Pro-Ile-Val-Gly-Lys-OH gave the following ratios: Asn 1.1; Ser 0.96; Gln 1.1; Pro 1.1; Gly 2.1; Val 0.80; Ile 0.78; Tyr 1.1Lys 1.1; in agreement with theory. Fast-atom bombardment mass spectrometry gave a molecular ion mass peak of 1288, in agreement with theory.

D. Labeling

The purified peptide was labeled with a fluorescent marker at the C-terminal end for use in the Pandex assay. $N^\alpha$-Biotin-Gly-Ser-Gln-Asn-Tyr-Pro-Ile-Val-Gly-Lys-OH (1.206 g, 0.936 mmol) was dissolved in 100 mL of 0.1M sodium borate, pH 9.5. Then, a solution of 3 g (7.7 mmol) of fluorescein isothiocyanate in 15 mL dimethyl sulfoxide was added to the reaction mixture in 10 equal portions over two hours. The resulting mixture was allowed to react for one hour after the final addition. The solution was adjusted to pH 3 using 5N hydrochloric acid, resulting in the formation of a precipitate which was removed by centrifugation.

The peptide solution was then adjusted to pH 7.8 using 5N sodium hydroxide and then diluted to 200 mL total volume by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5–25% acetonitrile, at 2 mL/minute, with collection of fractions. Analytical HPLC was used to analyze the fractions. The fractions containing the desired product were then combined, frozen and lyophilized to provide 190.2 mg (12%).

Amino acid analysis of the purified peptide gave the following: Asn 1.1; Ser 1.0; Gln 1.1; Pro 1.1; Gly 2.1; Val 0.8; Ile 0.8; Tyr 1.1; Lys 1.0; in agreement with theory. Fast-atom bombardment mass spectrometry gave a molecular ion mass peak of 1678, in agreement with theory.

E. Fluorescence HIV-1 Protease Inhibitor Assay

The following buffers and solutions are used in the Fluorescence HIV-1 Protease Inhibitor Assay:

| | |
|---|---|
| MES-ALB Buffer: | 0.05M 4-morpholineethane sulfonic acid, pH 5.5 |
| | 0.02M NaCl |
| | 0.002M EDTA |
| | 0.001M DTT |
| | 1.0 mg/mL BSA |
| TBSA Buffer: | 0.02M TRIS |
| | 0.15M NaCl |

| | 1.0 mg/mL BSA |
|---|---|
| Avidin Coated | |
| Beads Solution: | 0.1% solution of Fluoricon Avidin Assay Particles (Avidin conjugated to solid polystyrene beads, 0.6–0.8 microns in diameter in TBSA Buffer |
| Enzyme Solution: | 27 IU/mL of purified HIV-1 protease in MES-ALB buffer (1 IU equals the amount of enzyme required to hydrolyze 1 μmole of substrate per minute at 37° C. |

To each well of a round bottom, 96-well plate is added 20 μL of the Enzyme Solution followed by 10 μL of the compound to be evaluated in a 20% aqueous dimethylsulfoxide solution. Purified HIV-1 protease was obtained as described above. The resulting solution is incubated for one hour at room temperature and then 20 μL of a solution containing the substrate, $N^\alpha$-Biotin-Gly-Ser-Gln-Asn-Tyr-Pro-Ile-Val-Gly-Lys ($N^\epsilon$-FITC)—OH, in MES-ALB buffer (1.5 μl/ml) is added to each well. The solutions are then incubated for 16 hours at room temperature and then each well is diluted with 150 μL of MES-ALB buffer.

To each well of a second round bottom, 96-well Pandex plate is added 25 μL of the Avidin Coated Beads Solution. Then, to each well is added 25 μL of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The $IC_{50}$ results obtained in the Fluorescence Assay for the compounds of the present invention are set forth below in Table 1. All values have been normalized to a positive control which is [1S-(1R*,4R*,5S*)]-N-[1-(2-amino-2-oxoethyl)-2-oxo-3-aza-4-phenylmethyl-5-hydroxy-6-(2-(1-t-butylamino-1-oxomethyl)phenyl)hexyl)-2-quinolinyl carboxamide.

TABLE 1

Inhibitory Activity of Formula I Compounds

| Example No. | Fluorescence Assay $IC_{50}$ in ng/mL |
|---|---|
| Control | 1.0 |
| 1 | 0.16 |
| 2 | 0.99 |
| 3 | 0.88 |
| 4 | 9.8 |
| 5 | 0.16 |
| 6 | 1.5 |
| 7 | 0.72 |
| 8 | 11.2 |

We claim:
1. A compound of formula Ia

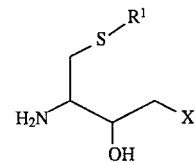

(IA)

wherein:
$R^1$ is aryl or $C_5$–$C_7$ cycloalkyl;
X is a group having the structure

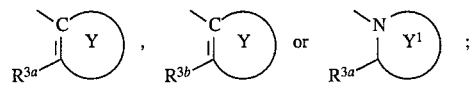

Y is aryl or unsaturated heterocycle;
$R^1$ is heterocycle;
$R^{3a}$ is a group having the structure:

1) $-C(O)-NR^4R^4$,

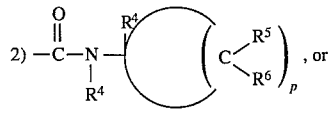

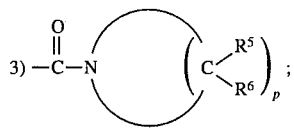

$R^{3b}$ is a group having the structure:

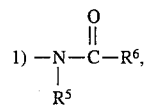

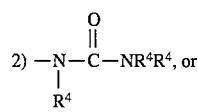

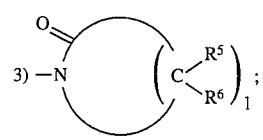

where
p is 4 or 5;
l is 3, 4 or 5;
$R^4$ at each occurrence is independently hydrogen, $C_1$–$C_6$ alkyl or hydroxy($C_1$–$C_4$)alkyl;
$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy($C_1$–$C_4$)alkyl, carboxy, $C_1$–$C_4$ alkoxycarbonyl, carbamoyl, N-($C_1$–$C_4$)alkylcarbamoyl, aryl, heterocycle or unsaturated heterocycle;
or a pharmaceutically acceptable salt thereof.

\* \* \* \* \*